United States Patent [19]

Von Sprecher et al.

[11] Patent Number: 4,785,004
[45] Date of Patent: Nov. 15, 1988

[54] AROMATIC THIOETHERS

[75] Inventors: Andreas Von Sprecher, Oberwil; Werner Breitenstein, Basel, both of Switzerland; Andreas Beck, Freiburg, Fed. Rep. of Germany; Robert W. Lang, Pratteln; Konrad Oertle, Therwil, both of Switzerland

[73] Assignee: Ciba-Geigy Corporation, Ardsley, N.Y.

[21] Appl. No.: 941,676

[22] Filed: Dec. 15, 1986

[30] Foreign Application Priority Data

Dec. 23, 1985 [CH] Switzerland .................. 5513/85
Apr. 4, 1986 [CH] Switzerland .................. 1321/86

[51] Int. Cl.[4] .................. C07C 149/40; A61K 31/235
[52] U.S. Cl. .................. 514/311; 514/312;
514/432; 514/456; 514/457; 514/513; 514/538;
514/539; 514/532; 514/544; 514/545; 514/546;
514/548; 514/562; 514/570; 514/571; 546/153;
546/156; 546/157; 549/23; 549/287; 549/289;
549/401; 549/402; 560/9; 560/17; 560/138;
560/142; 560/250; 560/254; 560/255; 562/426;
562/431
[58] Field of Search .................. 560/9, 17, 138, 142,
560/250, 254, 255; 562/426, 431; 558/257;
546/156, 158, 153, 165, 157; 549/23, 287, 289,
401, 402; 514/311, 312, 432, 456, 457, 513, 535,
544, 548, 538, 539, 532, 546, 562, 570, 571

[56] References Cited

U.S. PATENT DOCUMENTS 4,609,744 9/1986 Young .................. 549/402
4,649,215 3/1987 Sprecher .................. 560/152

FOREIGN PATENT DOCUMENTS 0123543 10/1984 European Pat. Off. .

*Primary Examiner*—Michael L. Shippen
*Attorney, Agent, or Firm*—Irving M. Fishman

[57] ABSTRACT

Novel asymmetric thioethers of the formula

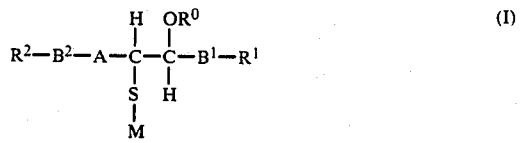

in which the general symbols have the following meanings:

$R^0$ represents hydrogen or $C_{1-7}$-alkanoyl,
$R^1$ represents $C_{1-3}$-alkyl which may be substituted by one or more halogen atoms having an atomic number of at most 17,
$R^2$ represents an aliphatic radical having from 5 to 15 carbon atoms,
A represents ethylene, a single bond or vinylene,
$B^1$ represents $C_{1-7}$-alkylene or phenylene,
$B^2$ represents a single bond, ethylene or phenylene, and
M represents an aromatic radical of the partial formula

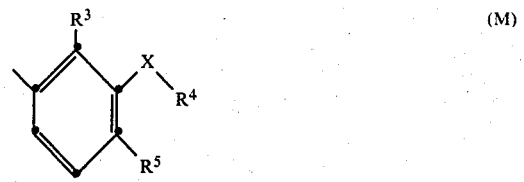

in which the symbols have the following meanings:
$R^3$ represents hydrogen or $C_{1-4}$-alkyl,
X represents NH, O, S or if $R^4$ represents hydrogen, a single bond,
one of the symbols $R^4$ and $R^5$ represents hydrogen and the other represents the group $—CO—R^6$, or
$R^4$ and $R^5$ together represent the radical $—CO—C(R^6)=C(R^7)$—or—$CO—C(R^7)=C(R^6)$—or
$R^4$ $R^5$, together with X, represent the radical $—N=C(R^8)—C(R^6)=CH—$, in which
$R^6$ represents $—(CH_2)_b—COOR^3$ (in which b=0 to 2)
$R^7$ represents hydrogen or $C_{1-4}$-alkyl and
$R^8$ represents hydrogen, methyl, mythoxy or halogen, and their salts are active as leucotriene antagonists since they eliminate the contractions of smooth muscles brought about by leucotrienes, and are therefore suitable for the treatment of allergic, especially asthmatic, conditions.

22 Claims, No Drawings

AROMATIC THIOETHERS

The invention relates to novel asymmetric α-hydroxy thioethers the sulphur atom of which is connected by one valency to an aromatic or heteroaromatic radical (M), such as a phenyl radical that is optionally substituted and/or condensed with a 6membered heterocyclic ring, and by the other valency to a linear radical (L) having at least 11 carbon atoms, which radical carries on one side of its chain, in the α-position to the sulphur atom, a hydroxy group that is preferably trans-orientated in relation to the S-atom, and on the other side may have one or more double bonds and/or a phenylene ring.

The invention relates especially to compounds of the formula $$R^2-B^2-A-\underset{\underset{\underset{M}{|}}{\overset{|}{S}}}{\overset{H}{C}}-\underset{\overset{|}{H}}{\overset{OR^0}{C}}-B^1-R^1 \quad (I)$$

in which the general symbols have the following meanings:

$R^0$ represents hydrogen or $C_{1-7}$-alkanoyl, $R^1$ represents $C_{1-3}$-alkyl which may be substituted by one or more halogen atoms having an atomic number of at most 17, $R^2$ represents an alihhatic radical having from 5 to 15 carbon atoms, A represents a single bond, ethylene or vinylene, $B^1$ represents $C_{1-7}$-alkylene or phenylene, $B^2$ represents a single bond, ethylene or phenylene, M represents an aromatic radical of the partial formula $$\text{(M)}$$

in which the symbols have the following meanings:

$R^3$ represents hydrogen or $C_{1-4}$-alkyl,

X represents NH, O, S or, if $R^4$ represents hydrogen, a single bond, one of the symbols $R^4$ and $R^5$ represents hydrogen and the other represents the group —CO—$R^6$, or $R^4$ and $R^5$ together represent the radical —CO—C($R^6$)=C($R^7$)— or —CO—C($R^7$)=C($R^6$)— or $R^4$ and $R^5$, together with X, represent the radical —N=C($R^8$)—C($R^6$)=CH—, in which $R^6$ represents —$(CH_2)_b$—$COOR^3$, in which b=0 to 2, $R^7$ represents hydrogen or $C_{1-4}$-alkyl and $R^8$ represents hydrogen, methyl, methoxy or halogen, and to salts of these compounds in so far as they have salt-forming properties.

The spatial representation in the above formula I for the preferred compounds, in which the O-atom of the hydroxy group is in the trans-configuration relative to the S-atom, is to be understood as follows: the symbols of the first line lie above, and those of the third line therefore below, the plane of representation (or vice versa), which for the formula shown corresponds to the relative configuration (RS)-(SR) of the two central carbon atoms according to the Kahn-Ingold-Prelog convention.

The invention relates also to processes for the manufacture of the above-defined compounds according to the invention, and to pharmaceutical compositions that contain these compounds as active ingredient, and to corresponding manufacturing processes by which such compositions are manufactured by non-chemical methods. The invention relates furthermore to the therapeutic use of the above-defined compounds and pharmaceutical compositions, especially in alleviating and eliminating those pathological conditions in which the pronounced leucotriene-antagonistic activity and/or phospholipase-inhibiting activity of the compounds according to the invention can be utilized, such as in the case of allergies of various types, especially in the case of asthma, and in the case of inflammation, especially of the skin and the mucosa.

A few years ago it was demonstrated (cf. H. R. Morris et al. Nature 285, 1045-1106 (May 1980) and L. Oerning, S. Hammarström and B. Samuelsson: Proc. Natl. Acad. Sci. USA 77 (4), 2014-2017 (1980)) that leucotrienes, especially leucotriene C and D, as a primary cause of a hypersensitivity reaction having immediate onset, are in all probability responsible for bronchial constriction in asthma.

The basic structural framework of leucotrienes in general is formed by a polyunsaturated linear icosanic acid which carries characteristic substituents in the 1-, 5- and 6-positions, as is shown by the formula below for the mentioned most important representatives:

LTC-4: $R^1$=HOCOCH($NH_2$)$CH_2CH_2$CO—; $R^2$=—$NHCH_2COOH$

LTD-4: $R^1$=H—; $R^2$=—$NHCH_2COOH$

LTE-4: $R^1$=H—; $R^2$=—OH

[Here, the spatial representation is to be understood as follows: the entire olefinic chain lies in the plane of representation and the valency lines indicated by arrows extend above the plane of representation whilst the broken lines extend below the plane.]

In their physiological properties, leucotrienes are in general distinguished by the fact that they cause a marked contraction of smooth muscle of the most varied kinds. From the standpoint of health such an effect is generally undesirable, and accordingly the search for suitable leucotriene antagonists is in the forefront of research in this field.

In the compounds of the formula I according to the invention, the basic linear framework of known leucotrienes is, in principle, retained and is combined, via the sulphur atom, with certain structural features that generally occur in aromatic and, especially, heteroaromatic compounds having blood coagulation-inhibiting properties. Surprisingly, in various test arrangements in vitro the novel compounds have a clear leucotriene-antagonistic action.

For example, in the tested concentration range of approximately from 0.1 to 25 μmol/1 they inhibit the contraction of a smooth muscle induced by leucotriene-$D_4$ ($LTD_4$ - see above). This so-called $LTD_4$-antagonism is demonstrated experimentally, for example, in the following manner: In segments taken from the ileum of a guinea pig weighing 300–400 g and incubated in an organ bath in Tyrode's solution at 38° C. whilst gassing with a mixture of 95% oxygen and 5% carbon dioxide at a load of 1 g, contractions are triggered with synthetic leucotriene-$D_4$ (in the form of a potassium salt) and isotonically registered. The extent of inhibition by the test substance is ascertained after a preliminary incubation of 2 minutes and evaluated as $IC_{50}$, that is to say the concentration that reduces the test contraction by 50%. The $LTD_4$-antagonism can also be demonstrated in vivo by a bronchoconstriction standard test on guinea pigs with aerosol administration. (The description of the test method is appended after the Examples.)

Surprisingly, compounds of the formula I also have a pronounced inhibiting effect on other physiologically important enzyme systems. For example, the inhibition of phospholipase $A_2$ from human leucocytes was observed in the tested concentration range of approximately from 0.5 to 50 μmol/1. (The experimental arrangement for this determination is described in detail in the appendix after the Examples.) Similarly, the inhibition of phospholipase C from human thrombocytes was observed in the tested concentration range of approximately from 1 to 100 μmol/1 (for the experimental arrangement see the appendix after the Examples).

The antiallergic and antiinflammatory properties indicated in vitro by these methods are also confirmed in animal tests in vivo. For example, the local antiinflammatory activity can be demonstrated, for example, according to the method developed by G. Tonelli and L. Thibault [Endocrinology 77, 625 (1965)], by inhibition of the oedema induced by croton oil in the ears of normal rats in a dosage range of from approximately 1 to approximately 100 mg/ml.

Owing to these valuable pharmacological properties, the compounds of the formula I according to the invention can be used therapeutically in all cases where the allergogenic action of leucotrienes leads to pathological conditions and is to be reduced or eliminated. Consequently, they can be used, for example, for the treatment of allergic conditions and diseases, such as, especially, asthma, but also hay fever and obstructive lung diseases, including cystic fibrosis. Similarly, owing to their antiinflammatory activity, they are suitable as inflammation-inhibiting agents, especially as external (topical) skin antiphlogistic agents for the treatment of inflammatory dermatoses of any kind, such as in the case of mild skin irritations, contact dermatitis, exanthema and burns, and as mucosa anti-phlogistic agents for the treatment of inflammations of the mucosa, for example of the eyes, nose, lips, mouth and genital or anal region. They can also be used as sun-screening agents. In addition, the high inhibiting activity on various blood factors suggests the possibility of therapeutic use of the compounds of the formula I in the thrombosis and blood coagulation indication range.

As already mentioned above, there is a general analogy between the structure of the compounds of the formula I according to the invention and that of leucotrienes, especially in the preferred transconfiguration of the vicinal S- and O-atoms mentioned at the beginning and in the linear structure of the radical (L). The latter differs, however, from leucotrienes in that it lacks the characteristic terminal carboxy group or that group is replaced by a varying number of halogen atoms. Also, in contrast to leucotrienes, the number, character and spatial arrangement of the multiple bonds in the radical (L) are not critical, since these bonds may even be missing or may be replaced by phenylene radicals. Also, the total length of the radical (L) is, within wide limits, incidental to the activity, and neither the absolute nor even the relative configuration of the two abovediscussed asymmetric carbon atoms is critical for the activity, as can be demonstrated, for example, with active 5(R),6(S)-epimers, which by comparison with natural leucotrienes have reverse absolute configuration of the carbon atoms 5 and 6 of the hydrocarbon chain (L).

Of the preferred meanings of $R^o$ in the formula I there may be mentioned, especially, hydrogen, and also $C_{1-4}$-alkanoyl, such as acetyl.

In the above-defined formula I, the symbol R1 represents, for example, an unsubstituted alkyl group, such as ethyl, propyl or, especially, methyl, or an analogous alkyl group substituted by chlorine or fluorine, especially at the terminal carbon atom, such as chloro- or fluoro-methyl, 2-fluoroethyl, or 3-fluoropropyl, or alternatively a perfluoroalkyl group, such as, especially, trifluoromethyl.

The aliphatic radical represented by the symbol $R^2$ is preferably a linear radical, for example an alkyl radical, consisting of from 5 to 15, preferably from 7 to 12, carbon atoms, such as, especially, heptyl, nonyl, undecyl and dodecyl, or a corresponding mono- or polyunsaturated radical that carries one, two or three multiple bonds, such as triple bonds and, especially, double bonds, in the cis- or trans-configuration as desired, in any combination. These multiple bonds are preferably as close as possible to the sulphur atom, that is to say in the $\alpha,\beta$-position to the sulphur-carrying carbon atom or conjugated with the vinylene radical represented by A. Preferred radicals $R^2$ of this type are, for example, 1-alkenyl, 1,3-alkadienyl and 1,3,6-alkatrienyl radicals, such as, especially, 1-heptenyl, 1-octenyl, 1-nonenyl, 1-decenyl, 1-undecenyl and 1-dodecenyl or 1,3-octadienyl, 1,3-decadienyl, 1,3-dodecadienyl and 1,3,6-dodecatrienyl, in which all of the double bonds can each individually be in cis- or trans-configuration and can form any combination.

The vinylene radical represented by the symbol A in formula I may be in the cis- or trans-configuration.

If $B^1$ in formula I represents a $C_{1-7}$-alkylene group, that group is preferably one of the partial formula —$(CH_2)_a$— in which a is equal to 1 to 7, preferably 2 to 4. If $B^1$ represents a phenylene group, that group is preferably m-phenylene; disregarding the radical $R^1$, it may additionally carry one or more $C_{1-4}$-alkyl radicals, especially methyl radicals, having a total of not more than 6 carbon atoms, but it is preferably unsubstituted.

The symbol $B^2$ in formula I preferably represents a single bond or a phenylene group, such as, especially, o- or p-phenylene; as in the case of the symbol $B^1$, the phenylene group may additionally carry alkyl radicals having a total of not more than 6 carbon atoms, but it is preferably unsubstituted. If $B^2$ represents phenylene, A preferably represents a single bond or vinylene.

The symbol $R^3$ defined in the formula I given at the beginning represents, on the one hand, as a constituent of the symbol $R^6$, preferably methyl and especially hydrogen; on the other hand, as the substituent of the phenyl ring, it preferably represents hydrogen or propyl.

Of the aromatic radicals of the partial formula (M), that is to say of these radicals in which the phenyl radical carries an aliphatic substituent in the m- or p-position, attention is drawn to those in which each of $R^3$ and $R^4$ represents hydrogen, X represents a single bond and $R^5$ represents the radical —CO—$(CH_2)_b$—COOR$^9$ (in which b preferably represents 2 and $R^9$ represents methyl, ethyl or, preferably, hydrogen) and especially to those in which each of $R^3$ and $R^5$ represents hydrogen, X represents the group —NH— and $R^4$ represents the radical —CO—$(CH_2)_b$-COOR$^9$ (in which b represents 0, 2 or, preferably, 1 and $R^9$ represents methyl, ethyl or, preferably, hydrogen), that is to say radicals of the partial formula

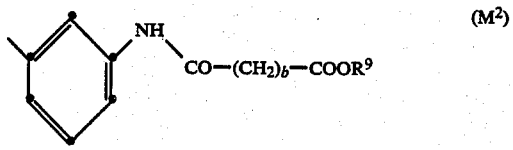 (M$^2$)

in which b and $R^9$ have the meanings given above.

Of the heteroaromatic radicals of the partial formula (M), attention is drawn especially to oxygen-containing radicals derived from chromene, especially those of the partial formula

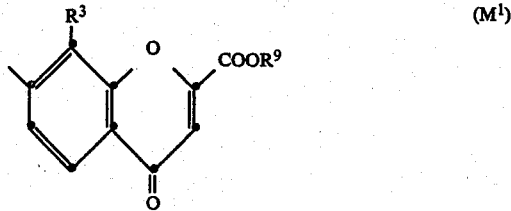 (M$^1$)

or also of the partial formula

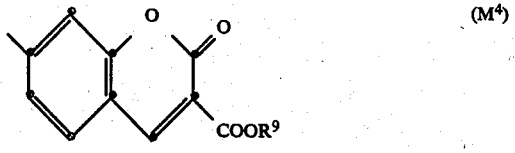 (M$^4$)

in which $R^3$ has the meanings given above and preferably represents propyl or especially hydrogen and $R^9$ represents ethyl or especially methyl and preferably hydrogen.

Of the heteroaromatic radicals of the partial formula (M) mention may also be made of nitrogen-containing radicals that are derived from quinoline and have the partial formula

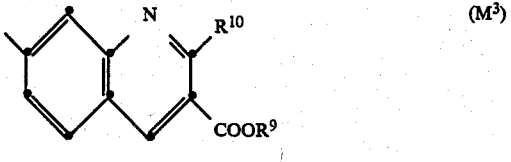 (M$^3$)

in which $R^9$ represents ethyl or especially methyl or also hydrogen, and $R^{10}$ represents halogen, such as, especially, chlorine or, more especially, methoxy.

These compounds to which attention has been drawn also include, as being especially preferred, those compounds in which the carboxy group is in the form of a salt, especially an alkali metal salt.

The remaining compounds of the formula I, depending on their individual character, can also be in the form of salts. Those that have adequate acidity, such as especially those having free carboxy groups, can form salts with bases, such as, especially, inorganic bases, preferably physiologically tolerable alkali metal salts, especially sodium and potassium salts. Those of the compounds of the formula I that have adequate basicity, such as esters of quinoline derivatives of the partial formula M$^3$ characterised above, can be in the form of acid addition salts, especially physiologically tolerable salts, with customary pharmaceutically acceptable acids; of the inorganic acids there may be mentioned especially hydrohalic acids, such as hydrochloric acid, and sulphuric acid and phosphoric or pyrophosphoric acid, and of the organic acids there may be mentioned especially sulphonic acids, for example aromatic sulphonic acids, such as benzene- or p toluenesulphonic acid, embonic acid and sulphanilic acid, or lower alkanesulphonic acids, such as methanesulphonic, ethanesulphonic, hydroxyethanesulphonic acid and ethylenedisulphonic acid, but also aliphatic, alicyclic, aromatic or heterocyclic carboxylic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic and p-aminosalicylic acid, as well as ascorbic acid. Compounds of the formula I that contain both basic and acidic functional groups, such as quinoline derivatives of the partial formula M$^3$ having a free carboxy group, can also be in the form of internal salts.

Of the compounds of the formula I according to the invention, attention is drawn to those in which the symbols have the following meanings: $R^o$ represents a $C_{1-4}$-alkanoyl group or, preferably, hydrogen; $R^1$ represents methyl, chloromethyl or trifluoromethyl; $R^2$ represents a linear alkyl radical having from 7 to 15 carbon atoms or a corresponding radical having 2, 3 or, preferably, one double bond(s), such as one of those mentioned above; A represents cis- or trans-vinylene; $B^1$ represents a linear alkylene group having from 2 to 5, preferably 2 or 3, carbon atoms; $B^2$ represents a single bond and M has one of the meanings given above under the partial formulae M$^2$, M$^3$ and, preferably, M$^1$; of these compounds attention is drawn very especially to those having a free carboxy group and to their pharmacologically tolerable salts, for example alkali metal salts, such as sodium and potassium salts.

Attention is also drawn to those compounds of the formula I in which the symbols have the following meanings: $R^o$ represents a $C_{1-4}$-alkanoyl group or preferably hydrogen; $R^1$ represents methyl, chloromethyl or trifluoromethyl; $R^2$ represents a linear alkyl radical having from 7 to 15, preferably from 8 to 12, carbon atoms, such as one of those mentioned above; A represents a single bond or vinylene in the cis- or trans-configuration; $B^1$ represents a linear alkylene group having from 2 to 5, preferably 2 or 3, carbon atoms; $B^2$ represents phenylene, especially o- or p-phenylene, and M has one of the meanings given above under the partial formulae $M^2$, $M^3$ and, preferably, $M^1$; of these compounds attention is drawn very especially to those having a free carboxy group and to their pharmacologically tolerable salts, for example alkali metal salts, such as sodium and potassium salts.

Attention is drawn especially to those compounds of the formula I in which the symbols have the following meanings: $R^o$ represents a $C_{1-4}$-alkanoyl group or preferably hydrogen; $R^1$ represents methyl, chloromethyl or trifluoromethyl; $R^2$ represents a linear alkyl radical having from 7 to 15 carbon atoms or a corresponding radical having 2, 3 or, preferably, one double bond(s), such as one of those mentioned above; A represents cis- or trans-vinylene; $B^1$ represents phenylene, especially m-phenylene; $B^2$ represents a single bond and M has one of the meanings given above under the partial formulae $M^2$, $M^3$ and, preferably, $M^1$; of these compounds attention is drawn most especially to those having a free carboxy group and to their pharmacologically tolerable salts, for example alkali metal salts, such as sodium and potassium salts.

Attention is also drawn especially to those compounds of the formula I in which the symbols have the following meanings: $R^o$ represents a $C_{1-4}$-alkanoyl group or preferably hydrogen; $R^1$ represents methyl, chloromethyl or trifluoromethyl; $R^2$ represents a linear alkyl radical having from 7 to 15, preferably from 8 to 12, carbon atoms, such as one of those mentioned above; A represents a single bond or, especially, vinylene in the cis- or trans-configuration; $B^1$ represents phenylene, especially m-phenylene; $B^2$ represents phenylene, especially o- or p-phenylene, and M has one of the meanings given above under the partial formulae $M^2$, $M^3$ and, preferably, $M^1$; of these compounds attention is drawn very especially to those having a free carboxy group and to their pharmacologically tolerable salts, for example alkali metal salts, such as sodium and potassium salts.

Attention is drawn more especially to the compounds of the formula I described in the Examples.

The thioethers according to the invention can be manufactured in a manner known per se, for example in the following manner: an aliphatic cis- or, preferably, trans-epoxide having a minimum of 11 carbon atoms and corresponding to the radical (L) defined at the beginning, especially of the formula

(II)

in which A, $B^1$, $B^2$, $R^1$ and $R^2$ have the meanings given above and in which, preferably, the two hydrogen atoms at the oxirane ring are trans-orientated with respect to one another, is reacted with a mercapto compound, corresponding to the above-defined radical (M), of the formula

H-S-M    (III)

in which M has the meaning mentioned above, or with a salt thereof, and, if necessary or desired, a resulting compound of the formula I in which $R^o$ represents hydrogen is acylated to a corresponding compound in which $R^o$ represents $C_{1-7}$-alkanoyl, and/or a compound present in the form of an ester is hydrolysed to the free acid or a salt thereof, and, if desired, a resulting free compound with salt-forming properties is converted into a salt thereof or a resulting salt is converted into a free compound.

The reaction is carried out under conditions known per se at temperatures of from approximately $-20°$ C. to approximately $+50°$ C., preferably at room temperature, and especially in a basic medium, for example in the presence of an amine, especially a tertiary aliphatic, arylaliphatic or saturated heterocyclic amine, such as trialkylamine (for example triethylamine or ethyldiisopropylamine), dialkylbenzylamine (for example N,N-dimethylbenzylamine), N,N-dialkylaniline (for example N,N-dimethylaniline) or N-methyl- or N-ethyl-piperidine or N,N'-dimethylpiperazine. Usually, the reaction is carried out in an inert organic solvent, such as a lower alkanol, for example methanol or ethanol.

The acylation of the hydroxy group formed in the main process, which may be carried out subsequently and which leads to compounds of the formula I in which $R^o$ represents $C_{1-7}$-alkanoyl, can be carried out in a manner known per se, for example by treatment of the primary product in which $R^o$ represents hydrogen with the desired acid, such as, for example, formic acid, or with a suitable reactive acid derivative, especially a halide (preferably chloride), symmetric anhydride, mixed anhydride (especially one with trifluoroacetic acid) or ketene. There may be used as reaction medium, for example, excess acylating agent, and also neutral, non-acylatable organic solvents, such as hydrocarbons (for example pentane, hexane, cyclohexane), halogenated hydrocarbons (for example methylene chloride, chloroform), ethers (for example diethyl ether, ethylene glycol dimethyl ether, tetrahydrofuran, dioxan), acid esters (for example ethyl acetate) and acid amides (for example acetamide, dimethylformamide); and optionally also non-acylatable organic bases of differing basicity, such as heteroaromatic bases (for example pyridine, collidine, quinoline), tertiary amines (for example triethylamine, N-ethylpiperidine, N-methylmorpholine, N,N'-dimethylpiperazine) or 1,5-diazabicyclo[5.4.0]undec-5-ene; alternatively the operation is carried out with advantageous combinations of all of these solvents. The reaction temperature may be in the range of approximately from $-70°$ to the boiling temperature of the mixture, preferably from approximately $-20°$ to approximately $+30°$ C.

In the main reaction (condensation with epoxide) the mercapto component of the formula III is used especially in the form of its $C_{1-4}$-alkyl ester (such as the methyl or ethyl ester); if the end product according to the invention is desired in the form of a free acid or its salt, then the resulting ester must be hydrolysed. The hydrolysis is carried out under the customary conditions, for example using alkali metal carbonates (for example sodium or potassium carbonate) or dilute alkali hydroxides (for example sodium or potassium hydroxide) in the presence of water in a water-miscible organic solvent, such as a lower alkanol (for example methanol or ethanol) or cyclic ethers (for example tetrahydrofuran or dioxan) at temperatures of approximately from 0° to 80° C., preferably at room temperature. In the case of especially sensitive compounds, it is possible to remove the ester group with retention of less alkali-stable groupings, such as those of ketocarboxylic acids, using even milder conditions, such as especially at low temperature (preferably below room temperature), with an equivalent stoichiometric amount of alkali, and using a shorter reaction time, optionally with analytical monitoring, for example by thin layer chromatography, but in the course of this operation an acylated hydroxy group in the radical R⁰ is generally removed at the same time.

Starting materials for the condensation process according to the invention are either known per se or can be obtained in a manner known per se according to known analogy processes. Thus, for example, the important mercapto compounds of the formula III have been described (cf. for example, EP-OL No. 0123543), and other analogous acids can be obtained in the same manner starting from corresponding known starting materials.

The cis- or preferably trans-epoxide used as starting material, for example that of the abovedefined formula II, can be manufactured especially by means of the same processes as those used in the synthesis of leucotrienes. For example, in a typical general method of synthesis, there is used as starting material an R¹-substituted benzaldehyde or a saturated aliphatic aldehyde (alkanal) of the formula

     (IV)

in which a and R¹ have the meanings given above.

This compound is condensed with formylmethylene-triphenylphosphorane (or an equivalent reagent), resulting in the corresponding α,β-unsaturated aldehyde, 2-trans-alkenal, of the formula

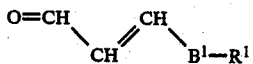     (V)

in which B¹ has the meanings given above. This compound is then epoxidised in a manner known per se, preferably under weakly alkaline conditions (for example in the presence of alkali carbonates), with aqueous hydrogen peroxide, resulting in a transepoxide, 2(RS),3(SR)-epoxy-alkanal of the formula

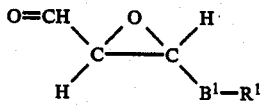     (VI)

in which B¹ has the meanings given above. In an analogous manner, an aldehyde having a cis-double bond yields the corresponding cis-epoxy configuration in the 2(RS),3(RS)-epoxyaldehyde. This epoxyaldehyde can be condensed to the desired transunsaturated epoxide, for example to that of the abovedefined formula II in which A represents the vinylene radical, by condensation with a corresponding known benzylidene or alkylidene triphenylphosphorane. For polyunsaturated epoxides, for example those of the formula II in which R² has one or more double bonds, there is an indirect alternative: instead of the Wittig reaction with an ylidene phosphorane unsaturated in its chain, the aldehyde IV is first lengthened by 4 carbon atoms with γ-triphenylphosphoranylidenebutyraldehyde (4-triphenyl-phosphoranylidenebutanal), epoxidised and only the resulting 4(RS),5(RS)-epoxy-2-alkenal is condensed with a single saturated alkylidene triphenylphosphorane or a less complicated benzylidene or alkenylidene triphenylphosphorane to the desired epoxide (for example one of the formula II). In the case of epoxides of the formula II in which A represents a single bond and B² represents phenylene, the aldehyde IV is reacted with a corresponding benzylidene triphenylphosphorane and subsequently epoxidised. In this case, however, usually a mixture of cis- and trans-styryl derivatives is formed, which must either be separated into the two individual isomers, or results in a mixture of the two isomeric epoxides from which then, in the main process, four stereoisomers may be formed.

If individual diastereoisomers are desired, then advantageously, at any stage, an individual diastereoisomer of a starting material can be used or a diastereoisomer can be formed preferentially from a racemic or optically inactive starting material by stereoselective reaction conditions or optically active reagents, or racemic diastereoisomeric mixtures can be separated by physical separation methods, optionally with the use of optically active auxiliaries, into optically individual diastereoisomers.

From the stereochemical point of view, however, both the condensation according to the invention of the formation components II and III, and the preparation of the starting materials, are especially carried out using in each case stereochemically uniform starting materials, carrying out the reactions as far as possible stereoselectively, for example by using optically active reagents and/or auxiliaries, and isolating stereochemically uniform products from the reaction mixtures directly after the reaction. Thus, for example, in the manufacture of the unsaturated starting materials, isomers with cis- and trans-double bonds that may be formed are immediately separated from one another, for which purpose the customary physical separation methods, such as, especially, chromatography, are suitable. In the main reaction, especially the epoxide of the formula II is used as an individual trans-stereoisomer, but in racemic form (which is the form normally obtained by the epoxidation of an olefin); the mercapto component of the formula III, if it is optically active, is preferably used in the form of an individual optical antipode - this measure makes it possible for the two optically active diastereoisomers formed to be separated from one another simply by customary physical methods, such as chromatography; if an optically inactive mercapto component is used, in order to obtain individual optically active products it is absolutely necessary to use the methods of cleaving into antipodes by means of optically active auxiliaries, such as, for example, the formation of salts with optically active bases. All suitable separation processes are known per se and can also be repeated or expediently combined with each other.

Owing to the close relationship between the novel compounds in free form and in the form of their salts, there are accordingly to be understood hereinbefore and hereinafter by the free compounds or their salts also the corresponding salts or free compounds, respectively.

The invention relates also to those embodiments of the process according to which a compound obtainable as intermediate at any stage of the process is used as starting material and the remaining steps are carried out, or a starting material is used in the form of a salt or is formed under the reaction conditions.

The invention relates also to the novel starting materials and intermediates produced in the processes according to the invention and the initial stages thereof.

The starting materials and the reaction conditions are preferably so selected that the compounds given special mention hereinbefore or listed as being especially preferred are obtained.

The present invention relates also to pharmaceutical compositions and medicaments that contain one of the compounds of the formula I according to the invention or a pharmaceutically acceptable salt thereof. The pharmaceutical compositions according to the invention are especially those which are intended for local administration and, especially, for inhalation administration, for example in the form of an aerosol, a micropulverised powder or a finely sprayed solution, to mammals, especially man, and which contain the active ingredient on its own or together with a pharmaceutically acceptable carrier.

Pharmaceutical preparations for topical and local use are, for example for the treatment of skin, lotions and creams that contain a liquid or semi-solid oil-in-water or water-in-oil emulsion, and ointments (these preferably containing a preservative). Suitable preparations for treatment of the eyes are eyedrops that contain the active compound in aqueous or oily solution, and eye ointments that are preferably manufactured in sterile form. Suitable preparations for the treatment of the nose are aerosols and sprays (similar to those described hereinafter for the treatment of the respiratory tract), coarse powders that are administered by rapid inhalation through the nostrils and, especially, nose drops that contain the active compound in aqueous or oily solution; suitable preparations for local treatment of the buccal cavity include lozenges that contain the active compound in a composition formed generally from sugar and gum arabic or tragacanth to which flavourings can be added, and pastilles that contain the active ingredient in an inert composition, for example consisting of gelatine and glycerine or sugar and gum arabic.

Suitable pharmaceutical compositions for administration in the form of aerosols or sprays are, for example, solutions, suspensions or emulsions of the active ingredient of the formula I according to the invention with a suitable pharmaceutically acceptable solvent, such as, especially, ethanol and water, or a mixture of such solvents. Depending on the requirements the compositions can also contain other pharmaceutical adjuncts, such as non-ionic or anionic surfactants, emulsifiers and stabilisers, as well as active ingredients of other kinds, and especially advantageously can be mixed with a propellant gas, such as an inert gas under elevated pressure, or, especially, with a readily volatile liquid that preferably boils under normal atmospheric pressure below the usual room temperature (for example from approximately −30° to +10° C.), such as an at least partially fluorinated polyhalogenated lower alkane, or with a mixture of such liquids. Such pharmaceutical compositions, which are predominantly used as intermediates or as stock mixtures for the manufacture of the corresponding medicaments in finished form, contain the active ingredient usually in a concentration of from approximately 0.1 to approximately 10%, especially from approximately 0.3 to approximately 3%, by weight. For the manufacture of medicaments in finished form, such a pharmaceutical composition is introduced into suitable containers, such as small bottles and pressurised bottles, which are provided with a spraying device or valve suitable for such purposes. The valve is preferably constructed as a metering valve which, on operation, releases a predetermined amount of liquid corresponding to a predetermined dose of the active ingredient. When manufacturing the finished medicament form, it is also possible for corresponding amounts of the pharmaceutical composition, in the form of stock solution, and of the propellant to be introduced separately into the containers and to be mixed only then. The dosage of the active ingredient of the formula I to be administered and the frequency of administration depend on the particular activity and on the duration of action of the individual compounds, on the severity of the illness to be treated and its symptoms, and on the sex, age, weight and individual responsiveness of the mammal to be treated. On average, the recommended daily dose of a compound of the formula I according to the invention for a mammal weighing 75 kg (especially man) is likely to lie within the range of from approximately 10 to approximately 500 mg, preferably from approximately 25 to approximately 250 mg, administration advantageously being effected in several doses per day as required.

The invention relates also to the use of the active ingredients of the formula I according to the invention for alleviating or eliminating pathological conditions and/or symptoms of the body of a mammal, especially man, that are attributable to the allergogenic action of leucotrienes and occur especially in the case of asthma. This use and the corresponding method of treatment is characterised by treating the affected body or part of the body with an antiallergically effective amount of a compound of the formula I on its own or in the form of a medicament, especially a pharmaceutical composition intended for inhalation. There is to be understood by "an antiallergically effective amount" that amount of the active ingredient which is sufficient to bring about significant inhibition of the contractions caused by leucotrienes.

The following Examples illustrate the present invention in more detail without limiting the scope thereof. All temperatures are quoted in degrees Celsius.

EXAMPLE 1

3-[5(S),6(R)-5-hydroxy-7-cis-pentadecen6-ylthio]-malonanilinic acid methyl ester and its 5(R),6(S)-stereoisomer.

6.2 ml of triethylamine and 1.2 g of 3-mercaptomalonanilinic acid methyl ester (EP-OL 0123543) are added to a solution of 1.1 g of 5(S),6(S)-5,6-epoxy-7-cis-pentadecene in 10 ml of methanol, the whole is stirred for 16 hours at room temperature and concentrated to dryness by evaporation in vacuo and the residue is chromatographed on silica gel with hexane/-ethyl acetate (3:2). The title compound is obtained in the form of a light-yellow oil, $[\alpha]_D^{20} = +3.3 \pm 1.6°$ (c=0.62 %, in chloroform).

In an analogous manner, the corresponding 5(R),6(R)-epoxide yields the stereoisomeric 3-[5(R),6(S)-5-hydroxy-7-cis-pentadecen-6-ylthio]-malonanilinic acid methyl ester.

The 5(S),6(S)-5,6-epoxy-7-cis-pentadecene used as starting material is manufactured, for example, in the following manner:

(a) 2-trans-heptenol 16.9 g of 2-heptinol in 200 ml of ether are added dropwise within a period of 30 minutes at 0° C., while stirring, to a solution of 10 g of lithium aluminium hydride in 400 ml of ether, and the resulting reaction mixture is boiled under reflux overnight. The excess LiAlH$_4$ is destroyed by the addition of 40 ml of ethyl acetate while cooling in an ice-water bath, and the resulting reaction mixture is taken up between ether and cold 1N sulphuric acid. The acidified (pH 2) aqueous layer is then extracted again with ether, and the combined organic extracts are dried over magnesium sulphate and concentrated by evaporation in vacuo. Distillation of the residue (18 g) under reduced pressure yields 13.2 g of 2-trans-heptenol in the form of a colourless oil, b.p. 71.5°–72° C./13 mbar.

(b) 2(R),3(R)-2,3-epoxyheptanol

Under anhydrous conditions, 25.7 g of 2-trans-heptenol (see above) and 140 ml of a 3.2M solution of tert.-butyl hydroperoxide in toluene are added in succession, at −23° C., to a stirred solution of 66.3 ml of tetraisopropyl orthotitanate and 38.51 ml of D-(−)-tartaric acid diethyl ester in 1.1 liters of methylene chloride, the whole is maintained for 16 hours at −20° C., and treated dropwise at −23° C. with 56 ml of a 10 % strength aqueous L-tartaric acid solution. After a further 30 minutes, the mixture is allowed to warm to +20° C. and further stirred until the organic layer can be separated off clearly. The latter is stirred for 1 hour with 1 liter of 1% strength aqueous sodium sulphite solution, separated off, washed with water, dried over sodium sulphate and concentrated in a water-jet vacuum. The residue is dissolved in 1.6 liters of diethyl ether, cooled to 0° C., 675 ml of N sodium hydroxide solution are added dropwise, and the whole is stirred for 30 minutes at 0° C. The organic phase, which has been separated off, is washed with saturated sodium chloride solution, dried and concentrated, yielding 2(R),3(R)-2,3-epoxyheptanol in the form of a colourless unstable liquid, which is immediately processed in the next stage.

The 2(S),3(S)-epimeric 2,3-epoxyheptanol can also be obtained in the following manner:

A solution of 2.28 g (20 mmol) of 2-trans-heptenol in 10 ml of methylene chloride is added at −20° C. to a solution of 5.94 ml of tetraisopropyl orthotitanate and 4.12 g of L-(+)-tartaric acid diethyl ester in 210 ml of methylene chloride, followed by 9.75 ml of a 4.1M solution of tert.-butyl hydroperoxide in 1,2-dichloroethane. The resulting reaction mixture is left to stand overnight at −20° C. After the addition of 8 ml of dimethyl sulphide, the whole is stirred for 45 minutes at from −20° to −23° C., then 50 ml of a 10 % strength aqueous solution of L-(+)-tartaric acid are added and the whole is further stirred for 30 minutes at −20° C and for 60 minutes without cooling. The organic phase is separated off, subsequently washed with 100 ml of water and, after having been dried over magnesium sulphate, concentrated by evaporation under reduced pressure. The residue, dissolved in 150 ml of ether, is stirred for 30 minutes at 0° C. with 60 ml of 1N NaOH, the aqueous phase is separated off and extracted again with ether, and the combined organic extracts are shaken with sodium chloride solution. The organic portion is dried over magnesium sulphate and the solvent is distilled off in vacuo to yield 2.3 g of 2(S),3(S)-2,3-epoxyheptanol in the form of a colourless unstable oil. It is immediately further processed.

(c) 2(S),3(R)-2,3-epoxyheptanal

A solution of 13.3 g of 2(R),3(R)-2,3-epoxyheptanol in 100 ml of methylene chloride is added dropwise within a period of 30 minutes to a stirred suspension of 110.1 g of pyridinium chlorochromate and 41.9 g of sodium acetate in 500 ml of methylene chloride, the temperature being maintained at 25° C. by cooling gently. After 3 hours, the reaction mixture is diluted with 500 ml of diethyl ether and filtered over silica gel. The filtrate is washed with phosphate buffer of pH 8, dried over sodium sulphate and concentrated by evaporation. Chromatography of the residue on silica gel with a mixture of petroleum ether (b.p. 30°–45°) and diethyl ether (3:2) yields 2(S),3(R)-2,3-epoxyheptanal in the form of a colourless liquid; the product has analogous spectral properties to those of its 2(R),3(S)-antipode (see the following).

The 2(R),3(S)-epimer can also be obtained in the following manner:

A solution of 1.2 g of 2(S),3(S)-2,3-epoxyheptanol in 28 ml of methylene chloride is added at room temperature to a freshly prepared solution of 5.5 g of chromium trioxide and 8.76 g of pyridine in 70 ml of methylene chloride and the resulting reaction mixture is further stirred for 30 minutes. The dark-coloured reaction mixture is decanted off from the material that has separated out, the latter is then washed with 160 ml of methylene chloride, and the combined organic portions are washed with 80 ml of phosphate buffer of pH 8.0. After drying over magnesium sulphate and concentration by evaporation under reduced pressure, the crude product that remains is chromatographed on 90 g of Merck silica gel 60 with toluene/ethyl acetate (4:1). 464 mg of 2(R),3(S)-2,3-epoxyheptanal are obtained in the form of a colourless oil. $[\alpha]_D^{20} = +101° \pm 1°$ (1.225 % in $CHCl_3$); IR ($CH_2Cl_2$): 2950, 2925, 2860, 2815, 2730, 1722, 1462, 1432, 1380, 1360, 1230, 1156, 850 cm$^{-1}$.

(d) 5(S),6(S)-5,6-epoxy-7-cis-pentadecene 0.31 ml of a 20 % solution of butyllithium in hexane is added dropwise at −78° C. under argon to a solution of 370 mg of octyltriphenylphosphonium bromide in 4.2 ml of tetrahydrofuran and 1.26 ml of hexamethylphosphoric acid triamide, and the resulting solution is stirred for a further 30 minutes at −78° C. A solution of 110 mg of 2(S),3(R)-2,3-epoxyheptanal in 1.0 ml of tetrahydrofuran is added dropwise at −78° C. to the resulting solution of triphenylphosphoranylideneoctene, and the reaction mixture obtained is stirred for a further 30 minutes at −78° C. For working up, the reaction mixture is partitioned between 100 ml of ether and 30 ml of phosphate buffer of pH 8.0, and the two phases are then extracted again with ether and buffer solution, respectively. The combined ethereal portions are dried over magnesium sulphate and concentrated by evaporation in vacuo, yielding 421 mg of oily crude product. This is stirred up with 2–3 ml of a 3:1 mixture of hexane and ether, the triphenylphosphine oxide precipitated in the form of crystals is separated off and the filtrate is concentrated by evaporation. The resulting residue (195 mg) is chromatographed on an aluminium oxide column (10 g), prepared in hexane with 0.5 % triethylamine, with the same eluant. 90.6 mg of the title compound are obtained in the form of a viscous yellowish oil.

The epimeric 5(R),6(R)-5,6-epoxy-7-cis-pentadecene is obtained in an analogous manner from the epimeric 2(R),3(S)-2,3-epoxyheptanol.

EXAMPLE 1A

3-[5(R),6(S)-5-hydroxy-7-cis-icosen-6-ylthio]-malonanilinic acid methyl ester

The title compound is obtained in an oily form in a manner analogous to that described in Example 1, but starting from 5(R),6(R)-5,6-epoxy-7-cis-icosene and 3-mercaptomalonanilinic acid methyl ester.

The 5(R),6(R)-5,6-epoxy-7-cis-icosene used as starting material can be obtained analogously to the method described in Example 1d by reacting 2(R),3(S)-2,3-epoxyheptanal with triphenylphosphoranylidene tridecene (produced from tridecyltriphenylphosphonium bromide with butyllithium).

EXAMPLE 1B

3-[5(S),6(R)-5-hydroxy-7-cis-icosen-6-ylthio]-malonanilinic acid methyl ester

The title compound is obtained in a manner analogous to that described in Example 1, but starting from 5(S),6(S)-epoxy-7-cis-icosene (produced analogously to Example 1A using 2(S),3(R)-2,3-epoxyheptanal) and 3-mercaptomalonanilinic acid methyl ester; IR ($CH_2Cl_2$): 2930, 2850, 1725, 1690, 1590, 1535, 1350 $cm^{-1}$.

EXAMPLE 2

7-[5(S),6(R)-5-hydroxy-7-cis-pentadecen6-ylthio]-4-oxo-4H-chromene-2-carboxylic acid methyl ester and its 5(R),6(S)-stereoisomer The title compound, $[\alpha]_D^{20} = -9.5° \pm 1.6°$ (c=0.63 % in chloroform), or its 5(R),6(S)-stereoisomer is obtained in a manner analogous to that described in Example 1, starting from 5(S),6(S)- or 5(R),6(R)-5,6-epoxy-7-cis-pentadecene, respectively, and 7-mercapto-4-oxo-4H-chromene-2-carboxylic acid methyl ester (EP-OL No. 0123543).

EXAMPLE 2A

7-[5(R),6(S)-5-hydroxy-7-cis-icosen-6-ylthio]-4-oxo-4H-chromene-2-carboxylic acid methyl ester The title compound is obtained in the form of a yellowish oil in a manner analogous to that described in Example 1, but starting from 5(R),6(R)-5,6-epoxy-7-cis-icosene (see Example 1A) and 7-mercapto-4-oxo-4H-chromene-2-carboxylic acid methyl eter.

EXAMPLE 2B

7-[5(S),6(R)-5-hydroxy-7-cis-icosen-6-ylthio]-4-oxo-4H-chromene-2-carboxylic acid methyl ester The title compound is obtained in a manner analogous to that described in Example 1, but starting from 5(S),6(S)-5,6-epoxy-7-cis-icosene (produced analogously to Example 1A using 2(S),3(R)-2,3-epoxyheptanal) and 7-mercapto-4-oxo-4H-chromene-2-carboxylic acid methyl ester; IR ($CH_2Cl_2$): 2930, 2860, 1750, 1660, 1600, 1415 $cm^{-1}$.

EXAMPLE 3

7-[5(S),6(R)-5-hydroxy-7-trans,9-cis-icosadiene-6-ylthio]-4-oxo-4H-chromene-2-carboxylic acid methyl ester The title compound is obtained in a manner analogous to that described in Example 1, starting from 5(S),6(S)-5,6-epoxy-7-trans,9-cis-icosadiene and 7-mercapto-4-oxo-4H-chromene-2-carboxylic acid methyl ester.

$[\alpha]_D^{20} = -97.4° \pm 0.9°$ (c=1.1% in chloroform).

The 5(S),6(S)-5,6-epoxy-7-trans,9-cis-icosadiene used as starting material is manufactured, for example, as follows:

(a) 4(S),5(S)-4,5-epoxy-2-trans-nonenal

A solution of 10 g of 2(R),3(S)-epoxyheptanal (see Example 1c) and 23.7 g of formylmethylenetriphenylphosphorane in 350 ml of chloroform is heated under reflux for 1.5 hours under argon. The cooled solution is freed of solvent at room temperature in vacuo and the residue is stirred up with ether/hexane (4:1). The suspension is filtered over a small amount of silica gel and washed with ether/hexane (4:1). The filtrate is concentrated in vacuo and the residue is chromatographed with hexane/ethyl acetate (5:1, with 1% triethylamine) on silica gel. The title compound is obtained in the form of a colourless oil.

(b) 5(S),6(S)-5,6-epoxy-7-trans,9-cis-icosadiene

The title compound is obtained in a manner analogous to that described in Example 1d by reacting 4(S),5(S)-4,5-epoxy-2-trans-nonenal with undecyltriphenylphosphonium bromide.

EXAMPLE 3A

3-[5(S),6(R)-5-hydroxy-7-trans,9-cis-icosadien-6-ylthio]-malonanilinic acid methyl ester The title compound is obtained in a manner analogous to that described in Example 1, but starting from 5(S),6(S)-5,6-epoxy-7-trans,9-cis-icosadiene (see Example 3b) and 3-mercaptomalonanilinic acid methyl ester.

EXAMPLE 4

7-5(R),6(S)-5-hydroxy-7,9-trans-11-cis-icosatrien-6-ylthio]-4-oxo-4H-chromene-2carboxylic acid methyl ester The title compound is obtained in a manner analogous to that described in Example 1, starting from 5(R),6(R)-5,6-epoxy-7,9-trans-11-cis-icosatriene and 7-mercapto-4-oxo-4H-chromene-2-carboxylic acid methyl ester; $[\alpha]_D^{20} = +198.9° \pm 2.7°$ (c=0.38% in $CHCl_3$), UV ($CHCl_3$): $\lambda max$ $^{(\epsilon)} = 268$ (34,100); 322 (11,900) nm.

The 5(R),6(R)-5,6-epoxy-7,9-trans-11-cisicosatriene used as starting material is manufactured, for example, in the following manner:

(a) 6(R),7(R)-6,7-epoxy-2,4-trans-undecadienal

A solution of 20.85 g of γ-triphenylphosphoranylidene crotonaldehyde in 200 ml of methylene chloride is added dropwise at 20° C., over a period of 1 hour, to a solution of 6.7 g of 2(S),3(R)-2,3-epoxyheptanal (see Example 1c) in 250 ml of methylene chloride, and the whole is stirred at 20° C. for a further 1 hour. The reaction mixture is diluted with 240 ml of hexane and 120 ml of ethyl acetate, filtered over silica gel and concentrated. The residue is taken up in equal volumes of hexane and ethyl acetate, stirred for 15 minutes and again filtered through silica gel and concentrated. For the purposes of isomerisation, the resulting oily mixture of cis,trans- and trans,trans-isomers is dissolved in 200 ml of methanol, then 220 mg of iodine are added and the whole is left to stand for 3 hours at 20° C. After washing with an aqueous sodium thiosulphate solution and water and drying over sodium sulphate, the solution is concentrated and the residue is chromatographed on silica gel. Elution with hexane/-ethyl acetate (4:1) yields the desired 6(R),7(R)-6,7-epoxy-2,4-trans-undecadienal in the form of a yellowish oil, $[\alpha]_D^{20} = -21.1° \pm 1.3°$ (0.75% w/v in chloroform) $\lambda_{max} = 276$ nm; $\epsilon = 29900$;

IR ($CH_2Cl_2$) 2950, 2920, 2850, 2800, 2720, 1678, 1640, 1600, 1460, 1163, 1120, 1007, 985 $cm^{-1}$.

(b) 5(R),6(R)-5,6-epoxy-7,9-trans-11-cis-icosatriene 6.85 ml of a 1.6M solution of butyllithium in toluene are added under argon to a stirred solution, cooled to −78° C., of 5.15 g of nonyltriphenylphosphonium bromide in 50 ml of tetrahydrofuran. After 30 minutes at −78° C., the mixture is treated dropwise in succession with 15.1 g of hexamethylphosphoric acid triamide and a solution of 1.52 g of 6(R),7(R)-6,7-epoxy-2,4-transundecadienal in 10 ml of tetrahydrofuran, and the whole is maintained for a further 15 minutes at −78° C. and allowed to warm to 0° C. Phosphate buffer (pH 8) is added to the reaction mixture and extraction with ether is carried out. The combined ethereal extracts are stabilised with a few drops of triethylamine, dried over sodium sulphate and freed of readily volatile components at 20° C. in vacuo. The residue is stirred up with small amounts of ether and the solid triphenylphosphine oxide that separates out is removed by filtration. The last portions of triphenylphosphine oxide are removed from the filtrate by filtration over a silica gel column, which has been prepared beforehand by washing out with a mixture (4:1) of ether/hexane having a 2% strength admixture of triethylamine. Removal of the solvent from the filtrate by distillation yields the desired product in the form of lightyellow crystals, m.p. 31°–32° C.

EXAMPLE 5

3-[5(S),6(R)-5-hydroxy-7-cis-pentadecen-6-ylthio]-malonanilinic acid 1.2 g of the methyl ester of the title compound (see Example 1) are dissolved in 30 ml of methanol, and 27 ml of 0.1N sodium hydroxide solution are added. The reaction mixture is stirred for 40 hours at room temperature and concentrated by evaporation in vacuo. The residue is filtered over silica gel with dichloromethane/methanol (9:1), the eluate is freed of eluant in vacuo, and the residue is dissolved in water and acidified with 1N hydrochloric acid. The aqueous phase is extracted with ether, and the extract is dried over magnesium sulphate, filtered and concentrated by evaporation. The title compound is obtained in the form of a white resin.

Rotational value of the sodium salt: $[\alpha]_D^{20} = +17.2° \pm 1.6°$ (c=0.65 %; methanol).

EXAMPLE 5A

3-[5(S),6(R)-5-hydroxy-7-trans,9-cis-icosadien-6-ylthio]-malonanilinic acid

The title compound is obtained in a manner analogous to that described in Example 5 from the corresponding methyl ester (see Example 3A); $]\alpha]_D^{20} = -24.2° \pm 0.9°$ (c=1.16 %; methanol); UV (methanol): $\lambda_{max}$ ($\epsilon$)=210 (sh); 240 (37240) nm.

EXAMPLE 6

7-[5(S),6(R)-5-hydroxy-7-cis-pentadecen-6-ylthio]-4-oxo-4H-chromene-2-carboxylic acid The title compound is obtained in a manner analogous to that described in Example 5, starting from the corresponding methyl ester $[\alpha]_D^{20} = +14.1° \pm 1.5°$ (c=0.68 %, methanol).

EXAMPLE 7

Sodium salt of 7-[5(R),6(S)-5-hydroxy-7,9-trans-11-cis-icosatrien-6-ylthio]-4-oxo-4H-chromene-2-carboxylic acid 1.1 g of the methyl ester of the title compound are dissolved in 30 ml of methanol, and 21 ml of 0.1N NaOH are added. The whole is stirred for 10 hours at room temperature, and the solution is concentrated in vacuo and chromatographed with methanol/water (3:1) over a reversed-phase column (Merck ready prepared column RP-8). The title compound is obtained in the form of a white resin. $[\alpha]_D^{20} = +145.8° \pm 2.6°$ (c=0.38 %; methanol). UV (methanol): $\lambda_{max}$ ($\epsilon$)=206 (23,500); 225 (23,360); 267 (34,340); 285 (sh); 324 (10,040) nm.

EXAMPLE 7A

Sodium salt of 3-[5(R),6(S)-5-hydroxy-7-cis-pentadecen-6-ylthio]-malonanilinic acid The title compound is obtained in a manner analogous to that described in Example 7 from the corresponding methyl ester (see Example 1); $[\alpha]_D^{20} = +13.8° \pm 2.8°$ (c =0.36 %; methanol).

UV (methanol): $\lambda_{max}$ ($\epsilon$)=223 (sh); 246 (18200) nm.

EXAMPLE 7B

Sodium salt of 7-[5(R),6(S)-5-hydroxy-7-cis-pentadecen-6-ylthio]-4-oxo-4H-chromene-2-carboxylic acid The title compound is obtained in a manner analogous to that described in Example 7 from the corresponding methyl ester (see Example 2); m.p., 246°–249°; $[\alpha]_D^{20} = 1.1° \pm 3.7°$ (c=0.27%; methanol). UV (methanol): $\lambda_{max}$ ($\epsilon$)=206 (22,200); 23 (19,800); 260 (sh); 267 (14,100); 324 (11,000) nm.

EXAMPLE 7C

Sodium salt of 7-[5(R),6(S)-5-hydroxy-7-cis-icosen-6-ylthio]-4-oxo-4H-chromene-2-carboxylic acid The title compound is obtained in a manner analogous to that described in Example 7 from the corresponding methyl ester (see Example 2A); $[\alpha]_D^{20} = 11.3° \pm 3.8°$ (c=0.27%; methanol).

EXAMPLE 7D

Sodium salt of 3-[5(R),6(S)-5-hydroxy-7-cis-icosen-6-ylthio]-malonanilinic acid

The title compound is obtained in a manner analogous to that described in Example 7 from the corresponding methyl ester (see Example 1A); $[\alpha]_D^{20} = -15.5° \pm 2.3°$ (c=0.43%; methanol); UV (methanol): $\lambda_{max}$ ($\epsilon$)=223 (sh); 246 (18,100) nm.

EXAMPLE 7E

Sodium salt of 7-[5(S),6(R)-5-hydroxy-7-cis-icosen-6-ylthio]-4-oxo-4H-chromene-2-carboxylic acid The title compound is obtained in a manner analogous to that described in Example 7 from the corresponding methyl ester (see Example 2B); UV (methanol): $\lambda_{max}$ ($\epsilon$)=324 (10,560), 266 (13,320), 223 (18,640).

EXAMPLE 7F

Sodium salt of 3-[5(S),6(R)-5-hydroxy-7-cis-icosen-6-ylthio]-malonanilinic acid The title compound is obtained in a manner analogous to that described in Example 7 from the corresponding methyl ester (see Example 1-B); $[\alpha]_D^{20} = +23.9° \pm 2.8°$ (0.36% in methanol).

EXAMPLE 8

Sodium salt of 7-[5(S),6(R)-5-hydroxy-7-trans,9-cis-icosadien-6-ylthio]-4-oxo-4H-chromene-2-carboxylic acid The title compound is obtained in a manner analogous to that described in Example 7 from the corresponding methyl ester. $[\alpha]_D^{20}32 -91 6° \pm 1°$ (0.8% in methanol).

EXAMPLE 9

7-[4(R),5(S)-1,1,1-trifluoro-4-hydroxy-6,10-cis,8-trans-nonadecatrien-5-ylthio]-4-oxo-4H-chromene-2-carboxylic acid methyl ester 0.74 g of triethylamine and then 0.58 g of 7-mercapto-4-oxo-4H-chromene-2-carboxylic acid methyl ester are added, while stirring and under argon, to a solution of 0.67 g of 4(R),5(R)-4,5-epoxy-1,1,1-trifluoro-6,10-cis,8-trans-nonadecatriene in 10 ml of methanol. The brown-red solution is stirred for 16 hours at 20° and concentrated by evaporation. The residue is chromatographed on silica gel with hexane/-ethyl acetate (7:3) and the title compound is obtained in the form of yellow crystals.

IR ($CH_2Cl_2$): 3020, 2970, 2940, 2860, 1750, 1670, 1610, 1420, 1150 $cm^{-1}$.

The 4(R),5(R)-4,5-epoxy-1,1,1-trifluoro-6,10-cis,8-trans-nonadecatriene used as starting material is manufactured, for example, as follows:

(a) 6,6,6-trifluoro-2-trans-hexenoic acid ethyl ester

Analogously to J. Am. Chem. Soc. 104, 3527-29 (1982), 3.42 g (10 mmol) of $Co_2(CO)_8$ in 50 ml of mesitylene are placed in a 0.3 liter autoclave at 0°; 0.5 mol of 3,3,3-trifluoropropene are introduced, followed at room temperature in succession by 65 bars of carbon monoxide and 65 bars of hydrogen. The reaction mixture is heated to 110° C. and, by the addition of a (1:1) mixture (v/v) of CO and $H_2$, the pressure is maintained constant at 130 bar. After absorption of the theoretical amount of the $CO/H_2$ mixture (1-5 hours), the whole is cooled to 0° and the autoclave is returned to normal pressure. To the crude mixture, which has been rinsed out with a small amount of mesitylene, there is slowly added, at room temperature, a solution of 156.8 g (0.45 mol) of ethoxycarbonylmethylenetriphenylphosphorane in 600 ml of methylene chloride. After the mildly exothermic reaction has subsided, the whole is stirred at room temperature for 2½ hours and then concentrated by evaporation. The residue is made into a slurry with pentane (approx. 100 ml), precipitated triphenylphosphine oxide is removed, and then distillation at reduced pressure is carried out. The desired ester is obtained in the form of a colourless oil (b.p. 78°-82°/26 mm Hg) in a yield of 50%.

(b) 6,6,6-trifluoro-2-trans-hexenol

A solution of 10 g of 6,6,6-trifluoro-2-transhexenoic acid ethyl ester (see above) in 70 ml of diethyl ether is cooled to 0°-5° and at this temperature 102 ml of 1M diisobutylaluminium hydride solution in hexane are added. The reaction mixture is then stirred for 5 minutes at 0°-5° and carefully hydrolysed with approx. 200 ml of 6N hydrochloric acid. The organic phase is separated off and the aqueous phase is extracted a further 3 times with ether. The combined organic phases are dried over $MgSO_4$, and concentrated by evaporation. Chromatography of the residue on silica gel with hexane/ethyl acetate (7:3) yields the title compound in the form of a colourless liquid.

(c) 2(R),3(R)-2,3-epoxy-6,6,6-trifluorohexanol

Under absolutely anhydrous conditions, a solution of 6.38 ml of tetraisopropyl orthotitanate and 4.5 ml of D-(−)-tartaric acid diethyl ester in 80 ml of $CH_2Cl_2$ is cooled to −70°. At this temperature 6.3 g of 6,6,6-trifluoro-2-trans-hexenol (see above) and 30.15 ml of 2.74M tert.-butyl hydroperoxide solution in toluene are added. The temperature is allowed to rise to 0° within a period of 2 hours and a solution of 27 g of iron(II) sulphate and 11 g of tartaric acid in 110 ml of water is added. After stirring for 30 minutes at 10°, the organic phase is separated off, the aqueous phase is extracted twice with ether, and the combined organic phases are dried over $Na_2SO_4$ and concentrated by evaporation. The residue is taken up in 120 ml of ether, cooled to 0°-5° and a suspension of 4.2 g of NaOH in 110 ml of saturated NaCl solution is added. The mixture is stirred for 1 hour at 0°-5°, the organic phase is separated off and the aqueous phase is extracted three times with ether. The combined organic phases are dried over $Na_2SO_4$ and concentrated by evaporation. The resulting title compound can be further processed without being further purified.

(d) 2(S),3(R)-2,3-epoxy-6,6,6-trifluorohexanal

A solution of 3.8 ml of oxalyl chloride in 40 ml of $CH_2Cl_2$ is cooled to −70° and 7 ml of dimethyl sulphoxide in 15 ml of $CH_2Cl_2$ are added dropwise, the temperature not exceeding −60°. After stirring for 10 minutes at −70°, 6.95 g of 2(R),3(R)-2,3-epoxy-6,6,6-trifluorohexanol (produced according to c) in 40 ml of $CH_2Cl_2$ are added dropwise within a period of 15 minutes. After a further 30 minutes at −70°, 28.7 ml of triethylamine are added dropwise and the temperature is allowed to rise to 0°. The reaction mixture is poured onto phosphate buffer (pH 8), the aqueous phase is extracted twice with $CH_2Cl_2$ and the combined organic phases are washed with water, dried over $Na_2SO_4$ and concentrated by evaporation. The resulting title compound is further processed directly.

(e) 6(R),7(R)-6,7-epoxy-10,10,10-trifluoro-2-trans,4-trans-decadienal and 6(R),7(R)-6,7-epoxy-10,10,10-trifluoro-2-trans,4-cis-decadienal A solution of 14.87 g of 4-triphenylphosphoranylidene croton aldehyde in 150 ml of $CH_2Cl_2$ is added dropwise within a period of 60 minutes to a solution of 6.87 g of 2(S),3(R)-2,3-epoxy-6,6,6-trifluorohexanal in 100 ml of $CH_2Cl_2$. The reaction mixture is stirred for a further 1 hour at 20° and concentrated by evaporation.

The residue is taken up in hexane/ethyl acetate (1:1) and filtered over silica gel. The filtrate is concentrated by evaporation and the residue is chromatographed on silica gel with hexane/ethyl acetate (4:1). Concentration by evaporation of the first fractions yields the 2-trans,4-cis-isomer of the title compound. The later fractions contain the 2-trans,4-trans-isomer of the title compound. Both products are yellow-brown oils.

(f) 4(R),5(R)-4,5-epoxy-1,1,1-trifluoro-6-cis,8-trans,10-cis-nonadecatriene

A stirred solution of 1.25 g of nonyltriphenylphosphonium bromide in 20 ml of tetrahydrofuran is cooled to −78° and, under argon, 1.66 ml of a 1.6M butyllithium solution in hexane is added. After 30 minutes at −78°, 4 g of hexamethylphosphoric acid triamide and then a solution of 0.45 g of 6(R),7(R)-6,7-epoxy-10,10,10-trifluoro-2-trans,4-cisdecadienal in a small amount of tetrahydrofuran are added dropwise. The whole is stirred for a further 15 minutes at −78°, the temperature is allowed to rise to 0°, phosphate buffer (pH 8) is added and extraction with ether is carried out. The combined organic phases are washed 3 times with phosphate buffer (pH 8), dried over $Na_2SO_4$ and concentrated by evaporation. The residue is suspended in a minimal amount of ether, freed of precipitated triphenylphosphine oxide by filtration, and concentrated by evaporation again. The resulting title compound is further processed directly in the main process.

EXAMPLE 10

7-[4(R),5(S)-1,1,1-trifluoro-4-hydroxy-6,8-trans,10-cis-nonadecatrien-5-ylthio]-4-oxo-4H-chromene-2-carboxylic acid methyl ester The title compound is obtained in a manner analogous to that described in Example 9 from 4(R),5(R)-4,5-epoxy-1,1,1-trifluoro-6,8-trans,10-cis-nonadecatriene and 7-mercapto-4-oxo-4H-chromene-2-carboxylic acid methyl ester.

IR ($CH_2Cl_2$): 3020, 2970, 2940, 2860, 1750, 1665, 1610, 1420, 139, 1150 $cm^{-1}$.

The 4(R),5(R)-4,5-epoxy-1,1,1-trifluoro-6,8-trans,10-cis-nonadecatriene used as starting material is manufactured, for example, in the following manner:

(a) The 6(R),7(R)-6,7-epoxy-10,10,10-trifluoro-2-trans,4-cis-decadienal obtained in Example 9e is reacted in a manner identical to that described in Example 9f and worked up to yield 4(R),5(R)-4,5-epoxy-1,1,1-trifluoro-6,8-trans,10-cis-nonadecatriene.

EXAMPLE 11

7-[4(S),5(R)-1,1,1-trifluoro-4-hydroxy-6,10-cis,8-trans-nonadecatrien-5-ylthio]-4-oxo-4H-chromene-2-carboxylic acid methyl ester The title compound is obtained in a manner analogous to that described in Example 9 from 4(S),5(S)-4,5-epoxy-1,1,1-trifluoro-6,10-cis,8-trans-nonadecatriene and 7-mercapto-4-oxo-4H-chromene-2-carboxylic acid methyl ester.

The 4(S),5(S)-4,5-epoxy-1,1,1-trifluoro-6,10cis,8-trans-nonadecatriene used as starting material is manufactured, for example, in the following manner:

(a) 2(S),3(S)-2,3-epoxy-6,6,6-trifluorohexanol

The title compound is obtained in the form of a colourless oil in a manner analogous to that described in Example 9c, but under the action of D-(+)-tartaric acid diethyl ester.

(b) 2(R),3(S)-2,3-epoxy-6,6,6-trifluorohexanal

The 2(S),3(S)-2,3-epoxy-6,6,6-trifluorohexanol from the preceding step is processed in a manner analogous to that described in Example 9d to yield the title compound.

(c) 6(S),7(S)-6,7-epoxy-10,10,10-trifluoro-2-trans,4-trans-decadienal and 6(S),7(S)-6,7-epoxy-10,10,10-trifluoro-2-trans,4-cis-decadienal In a manner analogous to that described in Example 9e, the 2(R),3(S)-2,3-epoxy-6,6,6-trifluorohexanal from stage 11b is processed to the isomeric mixture, which is separated by chromatography into the 2-trans,4-cis- and the 2-trans,4-trans-isomer.

(d) 4(S),5(S)-4,5-epoxy-1,1,1-trifluoro-6,10-cis,8-trans-nonadecatriene

The title compound is obtained in a manner analogous to that described in Example 9f by reacting 6(S),7(S)-6,7-epoxy-10,10,10-trifluoro-2-trans,4-cis-decadienal.

EXAMPLE 12

7-[4(S),5(R)-1,1,1-trifluoro-4-hydroxy-6,8-trans,10-cis-nonadecatrien-5-ylthio]-4-oxo-4H-chromene-2-carboxylic acid methyl ester The title compound is obtained in a manner analogous to that described in Example 9 from 7-mercapto-4-oxo-4H-chromene-2-carboxylic acid methyl ester and 4(S),5(S)-4,5-epoxy-1,1,1-trifluoro-6,8-trans,10-cis-nonadecatriene, which can be manufactured, by reaction analogously to Example 9f, from 6(S),7(S)-6,7-epoxy-10,10,10-trifluoro-2-trans,-4-trans-decadienal (see Example 11c).

EXAMPLE 12A

3-[4(R),5(S)-1,1,1-trifluoro-4-hydroxy-6-cis-icosen-5-ylthio]-malonanilinic acid methyl ester The title compound is obtained in a manner analogous to that described in Example 9 from 3-mercaptomalonanilinic acid methyl ester and 4(R),5(R)-4,5-epoxy-1,1,1-trifluoro-6-cis-icosene, which is obtained by reacting 2(S),3(R)-2,3-epoxy-6,6,6-trifluorohexanol with tetradecylphosphonium bromide analogously to Example 9f.

EXAMPLE 12B

7-[4(R),5(S)-1,1,1-trifluoro-4-hydroxy-6-cis-icosen-5-ylthio]-4-oxo-4H-chromene-2-carboxylic acid methyl ester The title compound is obtained in a manner analogous to that described in Example 9 from 7-mercapto-4-oxo-4H-chromene-2-carboxylic acid methyl ester and 2(S),3(R)-2,3-epoxy-6,6,6-trifluorohexanol.

EXAMPLE 12C

7-[4(R),5(S)-1,1,1-trifluoro-4-hydroxy-6-cis-icosen-5-ylthio]-2-methoxyquinoline-3-carboxylic acid methyl ester The title compound is obtained in a manner analogous to that described in Example 9 from 7-mercapto-2-methoxyquinoline-3-carboxylic acid methyl ester and 2(S),3(R)-2,3-epoxy-6,6,6-trifluorohexanol.

EXAMPLE 13

7-[4(R),5(S)-1,1,1-trifluoro-4-hydroxy-6,10-cis,8-trans-nonadecatrien-5-ylthio]-4-oxo-4H-chromene-2-carboxylic acid 0.35 g of the corresponding methyl ester (see Example 9) are dissolved in 40 ml of methanol, cooled to 0°, and 8 ml of 0.4N NaOH are slowly added. When the addition is complete the whole is allowed to warm to room temperature and stirred for a further 45 minutes. The methanol is evaporated off at room temperature, water and $CH_2Cl_2$ are added to the residue and the whole is acidified with cold 2N hydrochloric acid. The aqueous phase is separated off and then extracted twice with $CH_2Cl_2$ and the cmbined organic phases are dried over $MgSO_4$ and concentrated by evaporation. The title compound is obtained in the form of a brown-yellow viscous mass. IR ($CH_2Cl_2$): 3040, 2950, 2870, 1750, 1670, 1640, 1610, 1425, 1150 cm$^{-1}$.

EXAMPLE 14

7-[4(R),5(S)-1,1,1-trifluoro-4-hydroxy-6,8-trans,10-cis-nonadecatrien-5-ylthio]-4-oxo-4H-chromene-2-carboxylic acid The title compound is obtained in a manner analogous to that described in Example 13 from the corresponding methyl ester (see Example 10).

EXAMPLE 15

7-[4(S),5(R)-1,1,1-trifluoro-4-hydroxy-6,10-cis,8-trans-nonadecatrien-5-ylthio]-4-oxo-4H-chromene-2-carboxylic acid The title compound is obtained in a manner analogous to that described in Example 13 from the corresponding methyl ester (see Example 11).

EXAMPLE 16

7-[4(S),5(R)-1,1,1-trifluoro-4-hydroxy-6,8-trans,10-cis-nonadecatrien-5-ylthio]-4-oxo-4H-chromene-2-carboxylic acid The title compound is obtained in a manner analogous to that described in Example 13 from the corresponding methyl ester (see Example 12).

EXAMPLE 16A

Sodium salt of 3-[4(R),5(S)-1,1,1-trifluoro-4-hydroxy-6-cis-icosen-5-ylthio]-malonanilinic acid The title compound is obtained in a manner analogous to that described in Example 7 from the corresponding methyl ester (see Example 12A); $[\alpha]_D^{20} = -10.0 \pm 2.0°$ (0.5%; methanol).

EXAMPLE 16B

Sodium salt of 7-[4(R),5(S)-1,1,1-trifluoro-4-hydroxy-6-cis-icosen-5-ylthio]-4-oxo-4H-chromene-2-carboxylic acid The title compound is obtained in a manner analogous to that described in Example 7 from the corresponding methyl ester (see Example 12B); m.p. 243°–245°.

EXAMPLE 16C

Sodium salt of 7-[4(R),5(S)-1,1,1-trifluoro-4-hydroxy-6-cis-icosen-5-ylthio]-2-methoxyquinoline-3-carboxylic acid The title compound is obtained in a manner analogous to that described in Example 7 from the corresponding methyl ester (see Example 12C); UV (methanol): $\lambda_{max}$ ($\epsilon$)=332 (9300), 293 (7380), 226 (37960); $[\alpha]_D^{20} = -21.0 \pm 10.0°$ (0.1% in methanol).

EXAMPLE 17

7-[1(RS),2(SR)-2-hydroxy-1-(2-nonylphenyl)-hexylthio]-4-oxo-4H-chromene-2-carboxylic acid methyl ester A mixture of 2.42 g of 1(RS),2(RS)-1,2-epoxy-1-(2-nonylphenyl)-hexane, 1.77 g of 7-mercapto-4-oxo-4H-chromene-2-carboxylic acid methyl ester, 16 ml of triethylamine and 30 ml of methanol is stirred for 22 hours at room temperature under argon. The reaction mixture is then concentrated by evaporation under reduced pressure at room temperature and the residue is purified by chromatography on silica gel with $CH_2Cl_2$/acetone (98.5:1.5). 7-[1(RS),2(SR)-2-hydroxy-1-(2-nonylphenyl)-hexylthio]-4-oxo-4H-chromene-2-carboxylic acid methyl ester is obtained in the form of pale yellow solids having a melting point of 65°–68° C. IR ($CH_2Cl_2$): 3580, 2930, 2860, 1745, 1655, 1600, 1415, 1240, 1140 cm$^{-1}$.

The 1(RS),2(RS)-1,2-epoxy-1-(2-nonylphenyl)-hexane used as starting material can be obtained in the following manner:

(a) 1-(2-nonylphenyl)-1-hexanol

A third of a solution of 11 g of 2-nonylbromobenzene [cf. EP-OL 0 123 543] in 15 ml of tetrahydrofuran is added to a mixture, stirred under an argon atmosphere, of 1.1 g of magnesium chips, 8 ml of tetrahydrofuran and 3 drops of carbon tetrachloride and the whole is heated at the boil, under reflux, for 30 minutes. The remainder of the solution of 2-nonylbromobenzene is then added dropwise over a period of 35 minutes and the reaction mixture is maintained under reflux for 2 hours. After dilution with 15 ml of tetrahydrofuran, the suspension is cooled to −10° C. and added in portions to a solution, cooled to −70° C., of 4.6 g of hexanal in 12 ml of tetrahydrofuran. After stirring for 1 hour at −70° C., 200 ml of saturated aqueous ammonium chloride solution are added to the reaction mixture, the organic layer is separated off and the aqueous layer is extracted three times with ether. The residue that remains after the combined ethereal extracts have been dried and concentrated by evaporation is purified by chromatography on silica gel with mixtures of petroleum ether with an increasing amount of methylene chloride, yielding the desired 1-(2-nonylphenyl)-1-hexanol in the form of a colourless oil. IR ($CH_2Cl_2$): 3600, 2960, 2925, 2855, 1465 cm$^{-1}$.

(b) 1-(2-nonylphenyl)-1-trans-hexene

A mixture of 14.4 g of 1-(2-nonylphenyl)-1-hexanol, 2 g of toluene-4-sulphonic acid monohydrate and 250 ml of toluene is heated under reflux for 3 hours using a water separator. After cooling, the reaction mixture is washed twice with 10% strength (w/v) sodium bicarbonate solution and twice with water. The organic phase is dried over sodium sulphate and concentrated by evaporation in vacuo, and the residue is purified by chromatography on silica gel using hexane as eluant. The desired 1-(2-nonylphenyl)-transhexene is obtained in the form of a pale yellow oil. IR ($CH_2Cl_2$): 2960, 2930, 2855, 1465, 970 $cm^{-1}$.

(c) 1(RS),2(RS)-1,2-epoxy-1-(2-nonylphenyl)-hexane 15.2 g of 85% strength 3-chloroperbenzoic acid are added to a solution of 13.6 g of 1-(2-nonylphenyl)-1-trans-hexene in 350 ml of methylene chloride and the whole is stirred for 3 hours at room temperature. The reaction mixture is diluted with methylene chloride and washed twice in each case with saturated sodium bicarbonate solution and water. The semi-solid residue that remains after the organic phase has been dried and concentrated by evaporation is suspended in hexane and filtered, and the filtrate is concentrated by evaporation under reduced pressure. Chromatographic purification of the crude product on silica gel with hexane/ether (97:3) yields the desired 1(RS),2(RS)-1,2-epoxy-1-(2-nonylphenyl)-hexane in the form of a colourless oil. IR ($CH_2Cl_2$) 2960, 2930, 2860, 1470 $cm^{-1}$.

EXAMPLE 17A

7-[1(RS),2(SR)-1-(2-dodecylphenyl)-2hydroxypentylthio]-4-oxo-4H-chromene-2-carboxylic acid methyl ester The title compound is obtained in a manner analogous to that described in Example 17 but starting from 1(RS),2(RS)-1-(2-dodecylphenyl)-1,2-epoxypentane and 7-mercapto-4-oxo-4H-chromene-2-carboxylic acid methyl ester; m.p. 77°–78°; IR ($CH_2Cl_2$) 3580, 2960, 2925, 2855, 1745, 1655, 1600, 1415 $cm^{-1}$.

The 1(RS),2(RS)-1-(2-dodecylphenyl)-1,2-epoxypentane used as starting material can be manufactured according to the method described in Example 17a–c, as follows: 2-dodecylphenylmagnesium bromide and pentanal yield 1-(2-dodecylphenyl)-pentanol, which is dehydrated to 1-(2-dodecylphenyl)-pentene, and this is converted with 3-chloroperbenzoic acid to the desired epoxide (colourless oil, IR in $CH_2Cl_2$: 2960, 2920, 2850, 1460 $cm^{-1}$).

EXAMPLE 17B

7-[1(RS),2(SR)-2-hydroxy-1-(2-pentadecylphenyl)-pentylthio]-4-oxo-4H-chromene-2-carboxylic acid methyl ester The title compound is obtained in solid form (from petroleum ether) in a manner analogous to that described in Example 17, but starting from 1(RS),2(RS)-1,2-epoxy-1-(2-pentadecylphenyl)-pentane and 7-mercapto-4-oxo-4H-chromene-2-carboxylic acid methyl ester; m.p. 68°–69° C.; IR ($CH_2Cl_2$) 3580, 2960, 2930, 2860, 1745, 1655, 1600, 1415 $cm^{-1}$.

The 1(RS),2(RS)-1,2-epoxy-1-(2-pentadecylphenyl)-pentane used as starting material can be manufactured according to the method described in Example 17a–c, as follows: 2-pentadecylphenylmagnesium bromide and pentanal yield 1-(2-pentadecylphenyl)-pentanol, which is dehydrated to 1-(2-pentadecylphenyl)-pentene, and this is converted with 3-chloroperbenzoic acid to the desired epoxide.

EXAMPLE 17C

7-[1(RS),2(SR)-1-(2-dodecylphenyl)-2hydroxypentylthio]-4-oxo-8-propyl-4H-chromene-2-carboxylic acid methyl ester The title compound is obtained in the form of a viscous oil in a manner analogous to that described in Example 17, but starting from 1(RS),2(RS)-1-(2-dodecylphenyl)-1,2-epoxypentane (see Example 17A) and 7-mercapto-4-oxo-8-propyl-4H-chromene-2-carboxylic acid methyl ester; IR ($CH_2Cl_2$: 3580, 2960, 2930, 2860, 1745, 1655, 1590, 1410, 1250 $cm^{-1}$.

EXAMPLE 17D

7-[1(RS),2(SR)-2-hydroxy-1-(2-nonylphenyl)-hexylthio]-2-methoxyquinoline-3-carboxylic acid methyl ester The title compound is obtained in the form of a pale yellow honey in a manner analogous to that described in Example 17, but starting from 1(RS),2(RS)-1,2-epoxy-1-(2-nonylphenyl)-hexane (see Example 17c) and 7-mercapto-2-methoxyquinoline-3-carboxylic acid methyl ester; IR ($CH_2Cl_2$): 3580, 2950, 2920, 2850, 1725, 1610, 1480, 1450, 1400, 1340, 1190, 1080 $cm^{-1}$.

EXAMPLE 17E

7-[1(RS),2(SR)-1-(2-dodecylphenyl)-2hydroxypentylthio]-2-methoxyquinoline-3-carboxylic acid methyl ester The title compound is obtained in the form of a viscous oil in a manner analogous to that described in Example 17, but starting from 1(RS),2(RS)-1-(2-dodecyl-phenyl)-1,2-epoxypentane and 7-mercapto-2-methoxyquinoline-3-carboxylic acid methyl ester; IR ($CH_2Cl_2$): 3580, 2960, 2925, 2860, 1730, 1610, 1480, 1455, 1400, 1345, 1190, 1080 $cm^{-1}$.

EXAMPLE 17F

7-[1(RS),2(SR)-2-hydroxy-1-(2-pentadecylphenyl)-pentylthio]-2-methoxyquinoline-3-carboxylic acid methyl ester The title compound is obtained in the form of a viscous oil in a manner analogous to that described in Example 17, but starting from 1(RS),2(RS)-1,2-epoxy-1(2-pentadecylphenyl)-pentane and 7-mercapto-2-methoxyquinoline-3-carboxylic acid methyl ester; IR ($CH_2Cl_2$): 3580, 2960, 2925, 2850, 1730, 1610, 1480, 1455, 1400, 1340, 1080 $cm^{-1}$.

EXAMPLE 17G

7-[1(RS),2(SR)-2-hydroxy-1-(2-nonylphenyl)-pentylthio]-4-oxo-4H-chromene-2-carboxylic acid methyl ester The title compound is obtained in a manner analogous to that described in Example 17, but starting from 1(RS),2(RS)-1,2-epoxy-1-(2-nonylphenyl)-pentane and 7-mercapto-4-oxo-4H-chromene-2-carboxylic acid methyl ester; IR ($CH_2Cl_2$): 2930, 2860, 1745, 1660, 1605, 1240 $cm^{-1}$.

The 1(RS),2(RS)-1,2-epoxy-1-(2-nonylphenyl)pentane used as starting material can be manufactured analogously to Example 17a–c starting from 2-nonylbromobenzene and pentanol.

EXAMPLE 18

7-[1(RS),2(SR)-2-hydroxy-1-(2-nonylphenyl)-hexylthio]-4-oxo-4H-chromene-2-carboxylic acid A mixture of 2.5 g of 7-[1(RS),2(SR)-2-hydroxy-1-(2-nonylphenyl)-hexylthio]-4-oxo-4H-chromene-2-carboxylic acid methyl ester from Example 17, 100 ml of methanol and 55 ml of 0.1N aqueous sodium hydroxide solution is stirred for 18 hours at room temperature. The reaction mixture is concentrated by evaporation under reduced pressure at room temperature and the residue is partitioned between methylene chloride and 0.2N hydrochloric acid. The organic phase is washed with water and dried over sodium sulphate, and the solvent is removed at room temperature under reduced pressure. Recrystallisation of the solid residue from ether/hexane yields the title compound in the form of a pale yellow crystalline solid, m.p. 72°–75°.

IR (KBr): 3420 (broad), 2955, 2925, 2855, 1735, 1635, 1595, 1420, 1235, 1150, 960, 905, 760 cm$^{-1}$.

EXAMPLE 18A

7-[1(RS),2(SR)-1-(2-dodecylphenyl)-2-hydroxypentylthio]-4-oxo-4H-chromene-2-carboxylic acid The title compound is obtained from the corresponding methyl ester (see Example 17A) in a manner analogous to that described in Example 18; m.p. 111°–116°; IR (CH$_2$Cl$_2$): 3580, 3450, 2960, 2930, 2860, 1740, 1655, 1600, 1420 cm$^{-1}$.

EXAMPLE 18B

Sodium salt of 7-[1(RS),2(SR)-2-hydroxy-1-(2 pentadecylphenyl)-pentylthio]-4-oxo-4H-chromene-2-carboxylic acid The title compound is obtained in the form of a solid from the corresponding methyl ester (see Example 17B) in a manner analogous to that described in Example 18F below; m.p. 238°–240° (decomposition); IR (KBr): 2960, 2925, 2855, 1635, 1610, 1420 cm$^{-1}$.

EXAMPLE 18C

Sodium salt of 7-[1(RS),2(SR)-1-(2-dodecylphenyl)-2-hydroxypentylthio]-4-oxo-8-propyl-4H-chromene-2-carboxylic acid The title compound is obtained in solid form from the corresponding methyl ester (see Example 17C) in a manner analogous to that described in Example 18F below; m.p. 247°–249° (decomposition); IR (CH$_2$Cl$_2$): 2960, 2930, 2860, 1635, 1415, 1365 cm$^{-1}$.

EXAMPLE 18D

7-[1(RS),2(SR)-2-hydroxy-1-(2-nonylphenyl)-hexylthio]-2-methoxyquinoline-3-carboxylic acid A mixture of 1.1 g of 7-[1(RS),2(SR)-2-hydroxy-1-(2-nonylphenyl)-hexylthio]-2-methoxyquinoline-3-carboxylic acid methyl ester (see Example 17D), 35 ml of methanol and 2.5 ml of an aqueous 2N solution of sodium hydroxide is stirred for 14 hours at room temperature under argon and then concentrated under reduced pressure at 45°. The residue is acidified with 0.1N hydrochloric acid and taken up in methylene chloride. The organic extract is dried over sodium sulphate and concentrated in vacuo. The residue is chromatographed on silica gel and eluted with ether with an increasing amount of methanol. The solvent is distilled off to yield the title compound in the form of a pale yellow honey; IR (CH$_2$Cl$_2$): 3580, 3320, 2960, 2930, 2860, 1745, 1610, 1485, 1390, 1340 cm$^{-1}$.

EXAMPLE 18E

7-[1(RS),2(SR)-1-(2-dodecylphenyl)-2-hydroxypentylthio]-2-methoxyquinoline-3-carboxylic acid The title compound is obtained in the form of a yellowish resin from the corresponding methyl ester (see Example 17E) in a manner analogous to that described in Example 18D; IR (CH$_2$Cl$_2$): 3580, 3320, 2960, 2930, 2860, 1745, 1610, 1485, 1390, 1340 cm$^{-1}$.

EXAMPLE 18F

Sodium salt of 7-[1(RS),2(SR)-2-hydroxy-1-(2-pentadecylphenyl)-pentylthio]-2-methoxyquinoline-3-carboxylic acid 1.3 ml of an aqueous 1N solution of sodium -hydroxy-1-(2-pentadecylphenyl)-pentylthio]-2-methoxyquinoline-3-carboxylic acid methyl ester (0.81 g), 15 ml of methanol and 5 ml of tetrahydrofuran, and the whole is stirred for 12 hours at room temperature under argon. The readily volatile components are removed at 45° under reduced pressure and the residue is triturated with carbon tetrachloride. The volatile components are evaporated off in vacuo to yield the title compound in the form of a colourless solid having a melting point above 250°; IR (KBr): 2960, 2925, 2855, 1635, 1610, 1585, 1390, 1240 cm$^{-1}$.

EXAMPLE 18G

7-[1(RS),2(SR)-2-hydroxy-1-(2-nonylphenyl)-pentylthio]-4-oxo-4H-chromene-2-carboxylic acid The title compound is obtained from the corresponding methyl ester (see Example 17G) in a manner analogous to that described in Example 18; m.p. 124°–126°.

EXAMPLE 19

7-[1(RS),2(SR)-2-hydroxy-1-(4-nonylphenyl)-hexylthio]-4-oxo-4H-chromene-2-carboxylic acid methyl ester Under argon, 0.85 g of 1(RS),2(RS)-1,2-epoxy-1-(4-nonylphenyl)-hexane is dissolved in 20 ml of methanol; 0.86 g of triethylamine and then 0.85 g of 7-mercapto-4-oxo-4H-chromene-2-carboxylic acid methyl ester are added, and the whole is stirred at room temperature for 22 hours.

The precipitate that separates out is filtered off with suction and washed with a small amount of methanol and hexane. The resulting title compound melts at 135°–136°.

The 1(RS),2(RS)-1,2-epoxy-1-(4-nonylphenyl)-hexane used as starting material can be manufactured, for example, as follows:

(a) 1-(4-nonylphenyl)-hex-1-ene (mixture of cis-and trans-isomers)

A suspension of 13.9 g of pentyltriphenylphosphonium bromide in 150 ml of tetrahydrofuran is cooled to −20° under argon, 21.2 ml of 1.6M butyllithium solution in hexane are added within a period of 5 minutes and the whole is stirred for a further 30 minutes at 0°–10°. 6 g of 4-nonylbenzaldehyde in 40 ml of tetrahydrofuran are added dropwise over a period of 30 minutes to the mixture, which has been cooled to from −60° to −70°. The reaction mixture is allowed to warm spontaneously to 0°–10°, stirred at this temperature for a further 45 minutes and concentrated by evaporation.

The residue is taken up in hexane/ethyl acetate (1:1) and filtered over silica gel. The filtrate is concentrated by evaporation and chromatographed on silica gel with hexane. The title compound (mixture of cis- and trans-isomers) is obtained in the form of a colourless oil, which is used directly in the next stage.

(b) 1,2-epoxy-1-(4-nonylphenyl)-hexane and separation into the individual cis-[1(RS),2(SR)-] and trans-[1(RS),2(RS)-]-isomers 6.76 g of m-chloroperbenzoic acid (90% content) in 100 ml of dichloromethane are added to a solution of 6.32 g of 1-(4-nonylphenyl)-hex-1-ene (mixture of cis- and trans-isomers) from the preceding stage in 150 ml of dichloromethane while cooling to 0°–5°, and the whole is stirred for 20 hours at 20°. The reaction mixture is washed in succession with 10% strength (w/v) sodium sulphite solution, 5% strength (w/v) sodium carbonate solution and 3 portions of water, dried over sodium sulphate and concentrated by evaporation. Chromatography of the residue on silica gel with hexane/ethyl acetate (19:1) yields in succession the trans-[1(RS),2(RS)-] and the cis-[1(RS),2(SR)-]-isomer in the form of colourless oils.

EXAMPLE 19A

3-[1(RS),2(SR)-2-hydroxy-1-(4-nonylphenyl)-hexylthio]-malonanilinic acid methyl ester The title compound is obtained in a manner analogous to that described in Example 19, but starting from 1(RS),2(RS)-1,2-epoxy-1-(4-nonylphenyl)-hexane and 3-mercaptomalonanilinic acid methyl ester as mercapto component.

EXAMPLE 19B

7-[1(RS),2(SR)-2-hydroxy-1-(4-nonylphenyl)-hexylthio]-2-methoxyquinoline-3-carboxylic acid methyl ester The title compound is obtained in a manner analogous to that described in Example 19, but starting from 1(RS),2(RS)-1,2-epoxy-1-(4-nonylphenyl)-hexane and 7-mercapto-2-methoxyquinoline-3-carboxylic acid methyl ester as mercapto component.

EXAMPLE 20

7-[1(RS),2(RS)-2-hydroxy-1-(4-nonylphenyl)-hexylthio]-4-oxo-4H-chromene-2-carboxylic acid methyl ester In a manner analogous to that described in Example 19, but starting from the corresponding 1(RS),2(SR)-1,2-epoxy-1-(4-nonylphenyl)-hexane (see Example 19b), the title compound is obtained in the form of crystals, m.p. 85°–86°, after chromatography on silica gel and elution with hexane/ethyl acetate (3:2).

EXAMPLE 20A

7-[1(RS),2(SR)-2-hydroxy-1-(4-nonylphenyl)-pentylthio]-4-oxo-4H-chromene-2-carboxylic acid methyl ester In a manner analogous to that described in Example 19, but starting from 1(RS),2(RS)-1,2-epoxy-1-(4-nonylphenyl)-pentane and 7-mercapto-4oxo-4H-chromene-2-carboxylic acid methyl ester, the title compound is obtained in the form of yellow crystals having a melting point of 136°–138°.

The 1(RS),2(RS)-1,2-epoxy-1-(4-nonylphenyl)-pentane used as starting material can be manufactured analogously to Example 17a–c starting from 4-nonylbromobenzene and pentanal; IR (CH$_2$Cl$_2$): 2890, 2820, 1500, 1445 cm$^{-1}$.

EXAMPLE 21

Sodium salt of 7-[1(RS),2(SR)-2-hydroxy-1-(4-nonylphenyl)-hexylthio]-4-oxo-4H-chromene-2-carboxylic acid.

The title compound is obtained in the form of a solid from the corresponding methyl ester (see Example 19) in a manner analogous to that described in Example 7; m.p. 267° (decomposition).

EXAMPLE 22

Sodium salt of 7-[1(RS),2(SR)-2-hydroxy1-(4-nonylphenyl)-hexylthio]-malonanilinic acid The title compound is obtained in the form of a solid monohydrate from the corresponding methyl ester (see Example 19A) in a manner analogous to that described in Example 7; m.p. 168°–169°.

EXAMPLE 23

Sodium salt of 7-[1(RS),2(SR)-2-hydroxy-1-(4-nonylphenyl)-hexylthio]-2-methoxyquinoline-3-carboxylic acid The title compound is obtained in solid form from the corresponding methyl ester (see Example 19B) in a manner analogous to that described in Example 18F; m.p. 268°–270°.

EXAMPLE 24

Sodium salt of 7-[1(RS),2(SR)-2-hydroxy-1-(4-nonylphenyl)-hexylthio]-4-oxo-4H-chromene-2-carboxylic acid The title compound is obtained from the corresponding methyl ester (see Example 20) in a manner analogous to that described in Example 7.

EXAMPLE 24A

7-[1(RS),2(SR)-2-hydroxy-1-(4-nonylphenyl)-pentylthio]-4-oxo-4H-chromene-2-carboxylic acid The title compound is obtained from the corresponding methyl ester (see Example 20A) in a manner analogous to that described in Example 18; m.p. 98°–100°.

EXAMPLE 25

7-[1(RS),2(SR)-1-hydroxy-1-(m-tolyl)-3-trans-5-cis-pentadecadien-2-ylthio]-4-oxo-4H-chromene-2-carboxylic acid methyl ester A mixture of 2.2 g of 1(RS),2(RS)-1,2-epoxy-1-(m-tolyl)-3-trans-5-cis-pentadecadiene, 2.0 g of 7-mercapto-4-oxo-4H-chromene-2-carboxylic acid methyl ester and 3.4 ml of triethylamine in 40 ml of tetrahydrofuran is stirred at room temperature for 20 hours and freed of volatile components by distillation under reduced pressure. The residue is chromatographed on silica gel using as eluant a 3:2 mixture (v/v) of hexane/ethyl acetate to yield the title compound in the form of a red-yellow resin.

The 1(RS),2(RS)-1,2-epoxy-1-(m-tolyl)-3-trans-5-cis-pentadecadiene used as starting material can be manufactured in the following manner:

(a) 3-(m-tolyl)-2-trans-propenal (m-methylcinnamaldehyde)

A total of 152.1 g of formylmethylenetriphenylphosphorane is added in several portions to a boiling solution of 56.64 g of m-tolyl aldehyde in 670 ml of toluene, under reflux, and then the whole is heated at the boil for 16 hours. Volatile components are distilled off, and the residue is dissolved in a 4:1 mixture (v/v) of ether/hexane and filtered through silica gel. The filtrate is freed of the solvents by distillation, and distilled in a higher vacuum. The title compound is obtained in the form of a colourless oil, b.p. 87°–92°/3 mbar.

(b) 2(RS),3(SR)-2,3-epoxy-3-(m-tolyl)-propionaldehyde

A solution of 25.32 g of m-methylcinnamaldehyde (see above) in 400 ml of methanol is added dropwise over a period of 45 minutes, at 20°–25°, to a vigorously stirred mixture of 136 ml of 30% strength hydrogen peroxide and 54 g of sodium hydrogen carbonate in 1200 ml of water, and the whole is stirred for a further 2 hours. The reaction mixture is extracted several times with methylene chloride. The organic portions are washed once with a sodium sulphite solution, dried over sodium sulphate and freed of the solvent by evaporation. Chromatography of the residue on silica gel and elution with a 3:1 mixture (v/v) of hexane/ethyl acetate yields the title compound in the form of a colourless oil.

(c) 4(RS),5(RS)-4,5-epoxy-5-(m-tolyl)-2-transpentenal

A solution of 18.63 g of formylmethylenetriphenylphosphorane in 70 ml of methylene chloride is added dropwise at room temperature, under an argon atmosphere, to a solution of 9.56 g of 2(RS),3(SR)-2,3-epoxy-(m-tolyl)-propionaldehyde (see under b) in 50 ml of methylene chloride, and the whole is stirred at room temperature for 20 hours. The reaction mixture is concentrated, diluted with a mixture of hexane and ethyl acetate in a volumetric ratio of 1:1, and filtered over silica gel. Once the solvent has been evaporated off, the residue is chromatographed on silica gel. Elution with hexane/ether (1:1) and removal by distillation of the solvents yield the title compound in the form of a colourless oil.

(d) 1(RS),2(RS)-1,2-epoxy-1-(m-tolyl)-3-trans-5-cis-pentadecadiene

Under an argon atmosphere, 17.3 ml of a 1.6M solution of butyllithium in hexane are added to a stirred solution, cooled to −78°, of 13.39 g of decyltriphenylphosphonium bromide in 120 ml of tetrahydrofuran. The temperature of the mixture is temporarily allowed to rise spontaneously to 0° and then the solution is cooled again to −78°. While stirring and cooling, a solution of 7.02 g of 4(RS),5(RS)-4,5-epoxy-5-(m-tolyl)-2-trans-pentenal (see under c) in 30 ml of tetrahydrofuran is added dropwise in such a manner that the temperature does not exceed −70°. The reaction mixture is allowed to warm spontaneously to +10° and concentrated in vacuo. The residue is taken up in a 4:1 mixture (v/v) of ether/hexane and filtered through a silica gel column, which has been washed beforehand with the same solvent mixture with a 1% addition of triethylamine. Concentration of the filtrate in vacuo yields the title compound in the form of a colourless viscous oil.

EXAMPLE 25A

7-[1(RS),2(RS)-1-hydroxy-1-(4-methylphenyl)-3-cis-hexadecen-2-ylthio]-4-oxo-4H-chromene-2-carboxylic acid methyl ester The title compound is obtained in the form of yellow crystals, m.p. 133°–135°, in a manner analogous to that described in Example 25, but starting from 1(RS),2(RS)-1,2-epoxy-1-(4-methylphenyl)-3-cis-hexadecene and 7-mercapto-4-oxo-4H-chromene-2-carboxylic acid methyl ester.

The 1(RS),2(RS)-1,2-epoxy-1-(4-methylphenyl)-3-cis-hexadecene used as starting material can be manufactured according to the method described in Example 25a, b and d, as follows:

p-tolylaldehyde and formylmethylenetriphenylphosphorane yield p-methylcinnamaldehyde, which is reacted to form 2(RS),3(SR)-2,3-epoxy-3-(p-tolyl)propionaldehyde, and this is converted with tridecyltriphenylphosphonium bromide to the desired product; IR (CH$_2$Cl$_2$): 2880, 2810, 1490, 1445 cm$^{-1}$.

EXAMPLE 25B

7-[1(S),2(R)-1-hydroxy-1-(3-trifluoromethylphenyl)-4-(3-nonylphenyl)-3-cis-buten-2-ylthio]-4-oxo-4H-chromene-2-carboxylic acid methyl ester and its trans-isomer The title compounds are obtained in the form of a cis-/trans-isomeric mixture in a manner analogous to that described in Example 1, but starting from 1(S),2(S)-1-(3-trifluoromethylphenyl)-4-(3-nonylphenyl)-1,2-epoxy-3-butene (cis-/trans-isomeric mixture) and 7-mercapto-4-oxo-4H-chromene-2-carboxylic acid methyl ester. Chromatography on silica gel with hexane/ethyl acetate (7:3) results in separation of the isomers, the cis-isomer, $[\alpha]_D^{20} = +33.6° \pm 8.0°$ (0.125% in chloroform), being eluted before the trans-isomer, $[\alpha]_D^{20} = -183.0° \pm 7.4°$ (0.135% in chloroform).

The 1(S),2(S)-1-(3-trifluoromethylphenyl)-4-(3-nonylphenyl)-1,2-epoxy-3-butene used as starting material can be manufactured, for example, as follows:

(a) 3-(3-trifluoromethylphenyl)-2-trans-propenoic acid ethyl ester 88.9 g of ethoxycarbonylmethylenetriphenylphosphorane are added dropwise, while cooling, to a solution of 34.0 g of 3-trifluoromethylbenzaldehyde in 400 ml of dichloromethane. The reaction mixture is stirred for one hour at room temperature, the solvent is evaporated off in vacuo and the residue is filtered with ether/hexane (4:1) over silica gel. Concentration by evaporation of the eluate yields the title compound in the form of white crystals; m.p. 40°–41° C.

(b) 3-(3-trifluoromethylphenyl)-2-trans-propenol

Reduction of 3-(3-trifluoromethylphenyl)-2-trans-propenoic acid ethyl ester in the manner described in Example 9b yields the title compound in the form of a colourless oil; IR (CH$_2$Cl$_2$): 3550, 2820, 1310, 1140, 1100 cm$^{-1}$.

(c) 2(S),3(S)-2,3-epoxy-3-(3-trifluoromethylphenyl) propanol

Epoxidation of 3-(3-trifluoromethylphenyl)-2-trans-propenol in the manner described in Example 9c, but using L−(+)-tartaric acid diethyl ester, yields the title compound in the form of a colourless oil; IR (CH$_2$Cl$_2$): 3500, 2820, 1330, 1170, 1125, 1070 cm$^{-1}$.

(d)

2(R),3(S)-2,3-epoxy-3-(3-trifluoromethylphenyl)-propanol

Oxidation of 2(S),3(S)-2,3-epoxy-3-(3-trifluoromethylphenyl)-propanol in the manner described in EXAMPLE 9d yields the title compound in the form of a colourless oil; IR (CH$_2$Cl$_2$): 2820, 1730, 1330, 1170, 1125, 1070 cm$^{-1}$.

(e)

1(S),2(S)-1-(3-trifluoromethylphenyl)-4-(3-nonylphenyl)-1,2-epoxy-3-butene (cis-/trans-isomeric mixture)

In a manner analogous to that described in Example 1d, but starting from 2(R),3(S)-2,3-epoxy-3-(3-trifluoromethylphenyl)-propanol and 3-nonylbenzyltriphenylphosphonium bromide, the cis-/trans-isomeric mixture of the title compound is obtained in the form of a light-yellow oil.

EXAMPLE 25C

7-[1(S),2(R)-1-hydroxy-1-(3-trifluoromethylphenyl)-4-(3-nonylphenyl)-3-buten-2-ylthio]-2-methoxyquinoline-3-carboxylic acid methyl ester (cis-/trans-isomeric mixture)

The title compounds are obtained in the form of a colourless oil in a manner analogous to that described in Example 1, but starting from 1(S),2(S)-1-(3-trifluoromethylphenyl)-4-(3-nonylphenyl)-1,2-epoxy-3-butene (cis-/trans-isomeric mixture) and 7-mercapto-2-methoxyquinoline-3-carboxylic acid methyl ester; UV (chloroform): $\lambda_{max}$ ($\epsilon$)=340 (11 000) nm.

EXAMPLE 25D

7-[1(S),2(R)-1-hydroxy-1-(3-trifluoromethylphenyl)-4-(4-nonylphenyl)-3-cis-buten-2-ylthio]-4-oxo-4H-chromene-2-carboxylic acid methyl ester and its trans-isomer The title compounds are obtained in the form of a cis-/trans-isomeric mixture in a manner analogous to that described in Example 1, but starting from 1(S),2(S)-1-(3-trifluoromethylphenyl)-4-(4-nonylphenyl)-1,2-epoxy-3-butene (cis-/trans-isomeric mixture) and 7-mercapto-4-oxo-4H-chromene-2-carboxylic acid methyl ester. Chromatography with hexane/ethyl acetate (7:3) on silica gel results in separation of the isomers, the cis-isomer, [α]$_D^{20}$=+91.3°+8.7° (0.115% in chloroform), being eluted before the trans-isomer, [α]$_D^{20}$=−187.4°±7.4° (0.135% in chloroform).

The cis-/trans-isomeric mixture of 1(S),2(S)-1-(3-trifluoromethylphenyl)-4-(4-nonylphenyl)-1,2-epoxy-3-butene used as starting material is obtained in the form of a light-yellow oil in a manner analogous to that described in Example 1d, but starting from 2(R),3(S)-2,3-epoxy-3-(3-trifluoromethylphenyl)propanol and 4-nonylbenzyltriphenylphosphonium bromide.

EXAMPLE 25E

7-[1(S),2(R)-1-hydroxy-1-(3-trifluoromethylphenyl)-4-(4-nonylphenyl)-3-buten-2-ylthio]-2-methoxyquinoline-3-carboxylic acid methyl ester (cis-/trans-isomeric mixture)

The title compounds are obtained in the form of a colourless oil in a manner analogous to that described in Example 1, but starting from 1(S),2(S)-1-(3-trifluoromethylphenyl)-4-(4-nonylphenyl)-1,2-epoxy-3-butene (cis-/trans-isomeric mixture) and 7-mercapto-2-methoxyquinoline-3-carboxylic acid methyl ester; UV (chloroform): $\lambda_{max}$ ($\epsilon$)=340 (12 400), 300 (10,000) nm.

EXAMPLE 25F

7-[1(S),2(R)-1-hydroxy-1-(3-trifluoromethylphenyl)-3-trans-5-cis-hexadecadien-2-ylthio]-4-oxo-4H-chromene-2-carboxylic acid methyl ester The title compound is obtained in the form of a colourless oil in a manner analogous to that described in Example 1, but starting from 1(S),2(S)-1,2-epoxy-1-(3-trifluoromethylphenyl)-3-trans-5-cis-hexadecadiene and 7-mercapto-4-oxo-4H-chromene-2-carboxylic acid methyl ester; [α]$_D^{20}$=+49.4°±10° (0.099% in chloroform).

The 1(S),2(S)-1,2-epoxy-1-(3-trifluoromethylphenyl)-3-trans-5-cis-hexadecadiene used as starting material is obtained from 2(R),3(S)-2,3-epoxy-3-(3-trifluoromethylphenyl)-propanol (see Example 25B). This is vinylogized analogously to Example 25c, and reacted to form the required epoxide analogously to Example 25d, but using undecyltriphenylphosphonium bromide.

EXAMPLE 26

7-[1(RS),2(SR)-1-hydroxy-1-(m-tolyl)-3-trans-5-cis-pentadecadien-2-ylthio]-4-oxo-4H-chromene-2-carboxylic acid 6.6 ml of an aqueous 0.1N solution of sodium hydroxide are added to a solution of 3.02 g of the methyl ester of the title compound (see Example 25) in 50 ml of tetrahydrofuran, and the whole is stirred at 20° for 2 hours and concentrated under reduced pressure. The residue is dissolved in water, brought to pH 1 with 1N hydrochloric acid, and extracted with ether. The organic extracts are washed twice with a saturated sodium chloride solution, dried over magnesium sulphate and freed of solvent in vacuo. The residue is chromatographed on silica gel, and the fractions eluted with methylene chloride/methanol (5:1) yield the title compound in the form of an orange-coloured powder after the solvent has been distilled off; m.p. 66°–67°.

EXAMPLE 26A

Sodium salt of
7-[1(RS),2(SR)-1-hydroxy-1-(4-methylphenyl)-3-cis-hexadecen-2-ylthio]-4-oxo-4H-chromene-2-carboxylic acid.

The title compound is obtained from the corresponding methyl ester (see Example 25A) in a manner analogous to that described in Example 18F; m.p. 255°–257°.

EXAMPLE 26B

7-[1(S),2(R)-1-hydroxy-1-(3-trifluorothio]-4-oxo-4H-chromene-2-carboxylic acid

The title compound is obtained in the form of a beige solid in a manner analogous to that described in Example 5 starting from the corresponding methyl ester; m.p. 253° (decomposition).

EXAMPLE 26C

7-[1(S),2(R)-1-hydroxy-1-(3-trifluoromethylphenyl)-4-(3-nonylphenyl)-3-trans-buten-2-ylthio]-4-oxo-4H-chromene-2-carboxylic acid The title compound is obtained in the form of a light-yellow solid in a manner analogous to that described in Example 5 starting from the corresponding methyl ester; m.p. 253° (decomposition).

EXAMPLE 26D

7-[1(S),2(R)-1-hydroxy-1-(3-trifluoromethylphenyl)-4-(3-nonylphenyl)-3-buten-2-ylthio]-2-methoxyquinoline-3-carboxylic acid (cis-/transisomeric mixture)

The title compound is obtained in the form of a white solid in a manner analogous to that described in Example 5 starting from the corresponding cis-/trans-isomeric mixture of the methyl esters; m.p. 81°-82°.

EXAMPLE 26E

7-[1(S),2(R)-1-hydroxy-1-(3-trifluoromethylphenyl)-4-(4-nonylphenyl)-3-cis-buten-2-ylthio]-4-oxo-4H-chromene-3-carboxylic acid The title compound is obtained in the form of a solid in a manner analogous to that described in Example 5 starting from the corresponding methyl ester; m.p. 69°-70°.

EXAMPLE 26F

7-[1(S),2(R)-1-hydroxy-1-(3-trifluoromethylphenyl)-4-(4-nonylphenyl)-3-trans-buten-2-ylthio]-4-oxo-4H-chromene-2-carboxylic acid The title compound is obtained in the form of a solid in a manner analogous to that described in Example 5 starting from the corresponding methyl ester; m.p. 70°-71°.

EXAMPLE 26G

7-[1(S),2(R)-1-hydroxy-1-(3-trifluoromethylphenyl)-4-(4-nonylphenyl)-3-buten-2-ylthio]-2-methoxyquinoline-3-carboxylic acid (cis-/transisomeric mixture)

The title compounds are obtained in the form of a white solid in a manner analogous to that described in Example 5 starting from the corresponding cis-/trans-isomeric mixture of the methyl esters; m.p. 91°-92°.

EXAMPLE 26H

7-[1(S),2(R)-1-hydroxy-1-(3-trifluoromethylphenyl)-3-trans-5-cis-hexadecadien-2-ylthio]-4-oxo-4H-chromene-2-carboxylic acid The title compound is obtained in a manner analogous to that described in Example 18 from the corresponding methyl ester (see Example 25F); IR (CH$_2$Cl$_2$): 3620, 2930, 1650, 1605, 1330, 1130 cm$^{-1}$.

EXAMPLE 27

7-[1(RS),2(SR)-2-hydroxy-1-(3-nonylphenyl)-hexylthio]-4-oxo-4H-chromene-2-carboxylic acid methyl ester The title compound is obtained in the form of a yellowish powder, m.p. 92°-93°, in a manner analogous to that described in Example 17, but starting from 1(RS),2(RS)-1,2-epoxy-1-(3-nonylphenyl)-hexane and 7-mercapto-4-oxo-4H-chromene-2-carboxylic acid methyl ester.

The 1(RS),2(RS)-1,2-epoxy-1-(3-nonylphenyl)hexane used as starting material can be manufactured analogously to Example 17a–c starting from 3-nonylbromobenzene.

EXAMPLE 27A

7-[1(RS),2(SR)-2-hydroxy-1-(3-nonylphenyl)-pentylthio]-4-oxo-4H-chromene-2-carboxylic acid methyl ester The title compound is obtained in the form of light-yellow crystals, m.p..84°-86°, in a manner analogous to that described in Example 17, but starting from 1(RS),2(RS)-1,2-epoxy-1-(3-nonylphenyl)-pentane and 7-mercapto-4-oxo-4H-chromene-2-carboxylic acid methyl ester.

The 1(RS),2(RS)-1,2-epoxy-1-(3-nonylphenyl)pentane used as starting material can be manufactured analogously to Example 17a–c starting from 3-nonylbromobenzene and pentanal; IR (CH$_2$Cl$_2$): 2930, 2850, 1610, 1460 cm$^{-1}$.

EXAMPLE 28

3-[1(RS),2(SR)-2-hydroxy-1-(3-nonylphenyl)-hexylthio]-malonanilinic acid methyl ester The title compound is obtained in the form of a colourless oil in a manner analogous to that described in Example 1, but starting from 1(RS),2(RS)-1,2-epoxy-1-(3-nonylphenyl)-hexane (see Example 27) and 3-mercaptomalonanilinic acid methyl ester.

EXAMPLE 29

Sodium salt of 7-[1(RS),2(SR)-2-hydroxy-1-(3-nonylphenyl)-hexylthio]-4-oxo-4H-chromene-2-carboxylic acid The title compound is obtained in the form of a solid from the corresponding methyl ester (see Example 27) in a manner analogous to that described in Example 7; m.p. 185° (decomposition).

EXAMPLE 29A

7-[1(RS),2(SR)-2-hydroxy-1-(3-nonylphenyl)-pentylthio]-4-oxo-4H-chromene-2-carboxylic acid The title compound is obtained from the corresponding methyl ester (see Example 27A) in a manner analogous to that described in Example 18; m.p. 134°-136°.

EXAMPLE 30

Sodium salt of 3-[1(RS),2(SR)-2-hydroxy-1-(3-nonylphenyl)-hexylthio]-malonanilinic acid The title compound is obtained in the form of a solid from the corresponding methyl ester (see Example 28) in a manner analogous to that described in Example 7; m.p. 150°-152°.

EXAMPLE 31

7-[3(RS),4(SR)-4-hydroxy-1-(2-nonylphenyl)-1-trans-octen-3-ylthio]-4-oxo-4H-chromene-2-carboxylic acid methyl ester In a manner analogous to that described in Example 17, but starting from 3(RS),4(RS)-3,4-epoxy-1-(2-nonylphenyl)-1-trans-octene and 7-mercapto-4-oxo-4H-chromene-2-carboxylic acid methyl ester, the title compound is obtained in the form of a viscous oil after a 60 hour reaction time at room temperature and after customary working up; IR (CH$_2$Cl$_2$) 3590, 2960, 2930, 2860, 1750, 1655, 1600, 1420 cm$^{-1}$. According to $^1$H-

NMR analysis, the product contains approximately 10% of the corresponding cis-isomer.

The 3(RS),4(RS)-3,4-epoxy-1-(2-nonylphenyl)-1-trans-octene used as starting material can be produced in the following manner:

(a) 2-nonylbenzaldehyde

A third of a solution of 22 g of 2-nonylbromobenzene in 35 ml of tetrahydrofuran is added to a mixture, stirred under an argon atmosphere, of 3.4 g of magnesium chips, 25 ml of tetrahydrofuran and 3 drops of carbon tetrachloride and the whole is heated at the boil under reflux for 30 minutes. The remainder of the 2-nonylbromobenzene solution is then added dropwise over a period of one hour and the reaction mixture is maintained under reflux for 2 hours. After dilution with 40 ml of tetrahydrofuran the whole is cooled in an ice bath to approximately 5° and a solution of 11.6 ml of dimethylformamide in 20 ml of tetrahydrofuran is added dropwise over a period of 15 minutes. After stirring for one hour at room temperature, 250 ml of saturated ammonium chloride solution are added to the reaction mixture, the organic layer is separated off and the aqueous layer is extracted three times with ether. The residue that remains after the combined ethereal extracts have been dried and concentrated by evaporation is purified by chromatography on silica gel with mixtures of petroleum ether with an increasing amount of methylene chloride, yielding the desired 2-nonylbenzaldehyde in the form of a pale yellow liquid.

IR ($CH_2Cl_2$): 2920, 2850, 1695, 1600 cm$^{-1}$.

(b) 2-nonylbenzyl alcohol 0.57 g of sodium borohydride is added in portions, over a period of 15 minutes, to a stirred solution of 9.3 g of 2-nonylbenzaldehyde in 150 ml of methanol. After stirring for a further 30 minutes, the reaction mixture is concentrated by evaporation under reduced pressure and the residue is taken up in ether. The organic phase is washed with ice-cooled 0.2N hydrochloric acid and with water, dried over sodium sulphate and concentrated by evaporation in vacuo. Chromatographic purification of the residue on silica gel with mixtures of petroleum ether with an increasing amount of ether yields 2-nonylbenzyl alcohol in the form of a pale yellow oil.

IR ($CH_2Cl_2$): 3600, 2925, 2855, 1465, 1000 cm$^{-1}$.

(c) 2-nonylbenzyl bromide

A solution of 10 g of phosphorus tribromide in 50 ml of benzene is added dropwise over a period of 15 minutes to a stirred mixture of 6.6 g of 2-nonylbenzyl alcohol and 50 ml of benzene. The reaction mixture is heated under reflux for 30 minutes and, after cooling, ice-water and ether are added. The organic phase is separated off, washed with water, dried over sodium sulphate and concentrated by evaporation in vacuo. Chromatographic purification of the residue on silica gel with petroleum ether yields 2-nonylbenzyl bromide in the form of a colourless oil.

IR ($CH_2Cl_2$): 2920, 2850, 1470, 1210 cm$^{-1}$.

(d) 2-nonylbenzyltriphenylphosphonium bromide

A mixture of 7.2 g of 2-nonylbenzyl bromide, 5.77 g of triphenylphosphine and 60 ml of toluene is heated under reflux for 4 hours, cooled and diluted with 80 ml of ether. The 2-nonylbenzyltriphenylphosphonium bromide that separates out is removed by filtration, washed with ether and dried in vacuo; m.p. 174°–176°.

(e) 3(RS),4(RS)-3,4-epoxy-1-(2-nonylphenyl)-1-transoctene 6.4 ml of a 1.6M solution of butyllithium in hexane are added to a mixture, cooled to 5° and stirred under an argon atmosphere, of 5.6 g of 2-nonylbenzyltriphenylphosphonium bromide and 50 ml of absolute tetrahydrofuran. After a further 10 minutes a solution of 2(RS),3(RS)-2,3-epoxyheptanal in 15 ml of tetrahydrofuran is added dropwise within a period of 3 minutes. The mixture is stirred for a further one hour at 5° and for 15 minutes at room temperature, water is added and extraction is carried out three times with ether. The organic phase is dried over sodium sulphate and concentrated. The residue remaining is suspended in hexane and filtered, and the filtrate is concentrated by evaporation under reduced pressure. Chromatographic purification of the residue on silica gel and elution with a 97:3 mixture (v/v) of petroleum ether/ether yields 3(RS),4(RS)-3,4-epoxy-1-(2-nonylphenyl)-1-trans-octene;

IR ($CH_2Cl_2$) 2960, 2930, 2860, 1470, 870 cm$^{-1}$.

According to $^1$H-NMR analysis, the product contains approximately 10% of the corresponding cis-isomer.

Example 32

7-[3(RS),4(SR)-4-hydroxy-1-(2-nonylphenyl)-1-trans-octen-3-ylthio]-2-methoxyquinoline-3-carboxylic acid methyl ester The title compound is obtained in the form of a pale yellow oil in a manner analogous to that described in Example 17, but starting from 3(RS),4(RS)-3,4-epoxy-1-(2-nonylphenyl)-1-trans-octene (see Example 31e) and 7-mercapto-2-methoxyquinoline-3-carboxylic acid methyl ester; IR ($CH_2Cl_2$) 3580, 2960, 2925, 2860, 1730, 1615, 1485, 1460, 1400, 1345 cm$^{-1}$. According to $^1$H-NMR analysis the product contains approximately 10% of the corresponding cis-isomer.

EXAMPLE 33

7-[3(RS),4(SR)-4-hydroxy-1-(2-nonylphenyl)-1-trans-octen-3-ylthio]-4-oxo-4H-chromene-2-carboxylic acid The title compound is obtained in the form of a yellow honey from the corresponding methyl ester (eee Example 31) in a manner analogous to that described in Example 18; IR ($CH_2Cl_2$) 3580, 3450, 2960, 2925, 2860, 1740, 1655, 1600, 1415, 1240 cm$^{-1}$. According to $^1$H-NMR analysis the product contains approximately 10% of the corresponding cis-isomer.

EXAMPLE 34

7-[3(RS),4(SR)-4-hydroxy-1-(2-nonylphenyl)-1-trans-octen-3-ylthio]-2-methoxyquinoline-3-carboxylic acid The title compound is obtained in crystalline form from the corresponding methyl ester (see Example 32) in a manner analogous to that described in Example 18D; m.p. 65°–69°; IR ($CH_2Cl_2$): 3580, 3320, 2960, 2930, 2860, 1745, 1615, 1485, 1390, 1340, 1245 cm$^{-1}$. According to $^1$H-NMR analysis the product contains approximately 10% of the corresponding cis-isomer.

EXAMPLE 35

3-[3(RS),4(SR)-4-hydroxy-1-(4-octylphenyl)-1-octen-3-ylthio]-malonanilinic acid methyl ester (mixture of cis-/trans-isomers)

The title compound (mixture of cis-/transisomers) is obtained in a manner analogous to that described in Example 19A, but starting from 3(RS),4(RS)-3,4-epoxy-1-(4-octylphenyl)-1-octene (mixture of cis-/trans-isomers) and 3-mercaptomalonanilinic acid methyl ester as mercapto component.

(a) The 3(RS),4(RS)-3,4-epoxy-1-(4-octylphenyl)-1-octene used as starting material can be obtained according to the process described in Example 31e using 4-octylbenzyltriphenylphosphonium bromide.

EXAMPLE 36

Sodium salt of 3-[3(RS),4(SR)-4-hydroxy-1-(4-octylphenyl)-1-octen-3-ylthio]-malonanilinic acid (mixture of cis-/trans-isomers)

The title compound is obtained in semi-solid form from the corresponding methyl ester (mixture of cis-/trans-isomers) (see Example 35) in a manner analogous to that described in Example 7.

EXAMPLE 37

7-[3(RS),4(SR)-4-hydroxy-1-(4-octylphenyl)-1-octen-3-ylthio]-4-oxo-4H-chromene-2-carboxylic acid methyl ester (individual cis- and trans-isomer)

The title compound is obtained in the form of an isomeric mixture in a manner analogous to that described in Example 19, but starting from 3(RS),4(RS)-3,4-epoxy-1-(4-octylphenyl)-1-octene (mixture of cis-/trans-isomers) (see Example 35a) and 7-mercapto-4-oxo-4H-chromene-2-carboxylic acid methyl ester.

The product can be separated into individual components by chromatography on silica gel, first the cis-isomer and then the trans-isomer being obtained by elution with a 7:3 mixture (v/v) of hexane/ethyl acetate.

EXAMPLE 38

Sodium salt of 7-[3(RS),4(SR)-4-hydroxy-1-(4-octylphenyl)-1-trans-octen-3-ylthio]-4-oxo-4H-chromene-2-carboxylic acid The title compound is obtained from the corresponding methyl ester (trans-isomer, see Example 37) in a manner analogous to that described in Example 7.

EXAMPLE 39

Sodium salt of 7-[3(RS),4(SR)-4-hydroxy-1-(4-octylphenyl)-1-cis-octen-3-ylthio]-4-oxo-4H-chromene-2-carboxylic acid The title compound is obtained from the corresponding methyl ester (cis-isomer, see Example 37) in a manner analogous to that described in Example 7.

EXAMPLE 40

7-[1(RS),2(SR)-4-chloro-2-hydroxy-1-(2-nonylpheny)-butylthio]-4-oxo-4H-chromene-2-carboxylic acid methyl ester The title compound is obtained in the form of pale yellow crystals from ether/petroleum ether in a manner analogous to that described in Example 17, but starting from 1(RS),2(RS)-4-chloro-1,2-epoxy-1-(2-nonylphenyl)butane and 7-mercapto-4-oxo-4H-chromene-2-carboxylic acid methyl ester; m.p. 69°–73°; IR ($CH_2Cl_2$): 3580, 2960, 2930, 2860, 1745, 1655, 1605, 1420 $cm^{-1}$.

The 1(RS),2(RS)-4-chloro-1,2-epoxy-1-(2-nonylphenyl)-butane used as starting material can be manufactured as follows:

(a) 4-chloro-1-(2-nonylphenyl)-butanol

In a manner analogous to that described in Example 17a, but starting from 4-chlorobutyraldehyde, 2-nonylbromobenzene yields the title compound in the form of a colourless oil; IR ($CH_2Cl_2$): 3600, 2960, 2930, 2860, 1470, 1055 $cm^{-1}$.

(b) 4-chloro-1-(2-nonylphenyl)-1-trans-butene

In a manner analogous to that described in Example 17b, 4-chloro-1-(2-nonylphenyl)-butanol (see above) yields the title compound in the form of a colourless oil; IR ($CH_2Cl_2$): 2960, 2930, 2860, 1465, 970 $cm^{-1}$.

(c) 1(RS),2(RS)-4-chloro-1,2-epoxy-1-(2-nonylphenyl)butane

In a manner analogous to that described in Example 17c, 4-chloro-1-(2-nonylphenyl)-1-transbutene (see above) yields the title compound in the form of a colourless oil; IR ($CH_2Cl_2$) 2930, 2860, 1465, 1450 $cm^{-1}$.

EXAMPLE 40B

7-[1(RS),2(SR)-4-chloro-2-hydroxy-1-(2-nonylphenyl)-butylthio]-2-methoxyquinoline-3-carboxylic acid methyl ester The title compound is obtained in a manner analogous to that described in Example 40, but starting from 1(RS),2(RS)-4-chloro-1,2-epoxy-1-(2-nonylphenyl)butane and 7-mercapto-2-methoxyquinoline-3-carboxylic acid methyl ester; IR ($CH_2Cl_2$) 3580, 2960, 2935, 2860, 1730, 1615, 1485, 1080 $cm^{-1}$.

EXAMPLE 40B

7-[1(RS),2(SR)-6-chloro-2-hydroxy-1-(2-nonylphenyl)-hexylthio]-4-oxo-4H-chromene-2-carboxylic acid methyl ester The title compound is obtained in a manner analogous to that described in Example 40, but starting from 1(RS),2(RS)-6-chloro-1,2-epoxy-1-(2-nonylphenyl)hexane and 7-mercapto-4-oxo-4H-chromene-2-carboxylic acid methyl ester; m.p. 60°–62°.

The 1(RS),2(RS)-6-chloro-1,2-epoxy-1-(2-nonylphenyl)-hexane used as starting material can be manufactured according to the method described in Example 40a–c, as follows: 2-nonylphenylmagnesium bromide and 6-chlorohexanol yield 1-(2-nonylphenyl)-6-chlorohexanol, which is dehydrated to 1-(2-nonylphenyl)-6-chlorohexene, and this is converted with 3-chloroperbenzoic acid to the desired epoxide; IR ($CH_2Cl_2$) 2930, 2860, 1460, 1220, 900 $cm^{-1}$.

EXAMPLE 40C

7-[1(RS),2(SR)-6-chloro-2-hydroxy-1-(2-nonylphenyl)-hexylthio]-2-methoxyquinoline-3-carboxylic acid methyl ester The title compound is obtained in a manner analogous to that described in Example 40, but starting from 1(RS),2(RS)-6-chloro-1,2-epoxy-1-(2-nonylphenyl)hexane and 7-mercapto-2-methoxyquinoline-3-carboxylic acid methyl ester; IR (CH$_2$Cl$_2$): 3580, 2960, 2930, 2860, 1730, 1615, 1485, 1195, 1080 cm$^{-1}$.

EXAMPLE 40D

7-[1(RS),2(SR)-6-fluoro-2-hydroxy-1-(2-nonylphenyl)-hexylthio]-4-oxo-4H-chromene-2-carboxylic acid methyl ester The title compound is obtained in a manner analogous to that described in Example 40, but starting from 1(RS),2(RS)-6-fluoro-1,2-epoxy-1-(2-nonylphenyl)hexane and 7-mercapto-4-oxo-4H-chromene-2-carboxylic acid methyl ester; m.p. 60°–62°.

The 1(RS),2(RS)-1,2-epoxy-6-fluoro-1-(2-nonylphenyl)-hexane used as starting material can be manufactured, for example, as follows:

(a) 6-(2-nonylphenyl)-5-trans-hexenol 2.8 g of lithium aluminium hydride are added in portions over a period of 1 hour to a solution, stirred under a nitrogen atmosphere, of 34.4 g of 6-(2-nonylphenyl)-5-hexenoic acid methyl ester [EP-OL No. 0 123 543] in 300 ml of tetrahydrofuran. After a further 30 minutes, 30 ml of ethyl acetate and then 30 ml of water are added dropwise. The reaction mixture is acidified with 1N hydrochloric acid and extracted several times with ethyl acetate. The combined extracts are dried over sodium sulphate, concentrated by evaporation and chromatographed with dichloromethane on silica gel. The title compound is obtained in the form of a light-yellow oil; IR (CH$_2$Cl$_2$) 3620, 2930, 2850, 1470, 970 cm$^{-1}$.

(b) 6-fluoro-1-(2-nonylphenyl)-1-trans-hexene

A solution of 8.17 g of 6-(2-nonylphenyl)-5-trans-hexenol in 20 ml of dichloromethane is added dropwise over a period of 20 minutes, while cooling with ice, to a mixture, stirred under an argon atmosphere, of 4.68 g of diethylamino-sulphur trifluoride in 20 ml of dichloromethane. The whole is stirred for 14 hours at room temperature, water is added, and the organic layer is separated off and washed with saturated sodium bicarbonate solution and water. After drying and concentrating by evaporation, the crude product is purified by flash chromatography on silica gel with petroleum ether. The title compound is obtained in the form of a colourless oil; IR (CH$_2$Cl$_2$) 2930, 2850, 1465, 970 cm$^{-1}$.

(c) 1(RS),2(RS)-1,2-epoxy-6-fluoro-1-(2-nonylphenyl) hexane

Reaction of 6-fluoro-1-(2-nonylphenyl)-1-transhexene with 3-chloroperbenzoic acid in the manner described in Example 17c yields the title compound in the form of a colourless oil; IR (CH$_2$Cl$_2$) 2920, 2850, 1455 cm$^{-1}$.

EXAMPLE 40E

7-[1(RS),2(SR)-6-fluoro-2-hydroxy-1-(2-nonylphenyl)-hexylthio]-2-methoxyquinoline-3-carboxylic acid methyl ester The title compound is obtained in a manner analogous to that described in Example 40, but starting from 1(RS),2(RS)-6-fluoro-1,2-epoxy-1-(2-nonylphenyl)hexane and 7-mercapto-2-methoxyquinoline-3-carboxylic acid methyl ester; IR (CH$_2$Cl$_2$) 3580, 2925, 2860, 1730, 1615, 1485, 1195, 1080 cm$^{-1}$.

EXAMPLE 41

7-[1(RS),2(SR)-4-chloro-2-hydroxy-1-(2-nonylphenyl)-butylthio]-4-oxo-4H-chromene-2-carboxylic acid The title compound is obtained in the form of pale yellow crystals from the corresponding methyl ester (see Example 40) in a manner analogous to that described in Example 18; m.p. 136°–138°; IR (CH$_2$Cl$_2$) 3580, 3430, 2925, 2860, 1735, 1645, 1600, 1420 cm$^{-1}$.

EXAMPLE 42

Sodium salt of 7-[1(RS),2(SR)-4-chloro-2-hydroxy-1-(2-nonylphenyl)-butylthio]-2-methoxyquinoline-3-carboxylic acid The title compound is obtained from the corresponding methyl ester (see Example 40A) in a manner analogous to that described in Example 18F; m.p. 187°–192°.

EXAMPLE 43

7-[1(RS),2(SR)-6-chloro-2-hydroxy-1-(2-nonylphenyl)-hexylthio]-4-oxo-4H-chromene-2-carboxylic acid The title compound is obtained from the corresponding methyl ester (see Example 40B) in a manner analogous to that described in Example 18; m.p. 135°–139°.

EXAMPLE 44

7-[1(RS),2(SR)-6-chloro-2-hydroxy-1-(2-nonylphenyl)-hexylthio]-2-methoxyquinoline-3-carboxylic acid The title compound is obtained from the corresponding methyl ester (see Example 40C) in a manner analogous to that described in Example 18; IR (CH$_2$Cl$_2$) 3570, 3300, 2960, 2920, 2850, 1740, 1610, 1480, 1240 cm$^{-1}$.

EXAMPLE 45

7-[1(RS),2(SR)-6-fluoro-2-hydroxy-1-(2-nonylphenyl)-hexylthio]-4-oxo-4H-chromene-2-carboxylic acid The title compound is obtained from the corresponding methyl ester (see Example 40D) in a manner analogous to that described in Example 18; IR (CH$_2$Cl$_2$) 3580, 2900 (broad), 2960, 2930, 1740, 1660, 1630, 1600, 1420 cm$^{-1}$.

EXAMPLE 46

7-[1(RS),2(SR)-6-fluoro-2-hydroxy-1-(2-nonylphenyl)-hexylthio]-2-methoxyquinoline-3-carboxylic acid The title compound is obtained from the corresponding methyl ester (see Example 40E) in a manner analogous to that described in Example 18; IR (CH$_2$Cl$_2$): 3580, 2960, 2930, 2820, 1745, 1615, 1490, 1390, 1340, 1245 cm$^{-1}$.

EXAMPLE 47

7-[1(S),2(R)-1-hydroxy-1-(m-tolyl)-3-trans-5-cis-pentadecadien-2-ylthio]-4-oxo-4H-chromene-2-carboxylic acid methyl ester and its 1(R),2(S)-diastereoisomer The title compounds are obtained in a manner analogous to that described in Example 25, but starting from the pure diastereoisomeric epoxides; 1(S),2(R)-diastereoisomer: [α]$_D^{20}$=−50.9°±9° (0.11% in chloroform), and 1(R),2(S)-diastereoisomer:

The 1(S),2(S)-1,2-epoxy-1-(m-tolyl)-3-trans-5-cis-pentadecadiene and its 1(R),2(R)-diastereoisomer, used as starting material, are obtained analogously to Example 25c and d, but using the corresponding pure diastereoisomeric aldehydes, that is to say 2(R),3(S)-2,3-epoxy-3-(m-tolyl)-propanal and its 2(S),3(R)-stereoisomer. These are obtained analogously to Example 25B (a-d), but starting from m-tolualdehyde using L—(+)-tartaric acid diethyl ester and D-(—)tartaric acid diethyl ester, respectively, in the epoxidation.

EXAMPLE 48

7-[1(S),2(R)-1-hydroxy-1-(m-tolyl)-3-trans-5-cis-pentadecadien-2-ylthio]-4-oxo-4H-chromene-2-carboxylic acid and its 1(R),2(S)-diastereoisomer The title compounds are obtained from the corresponding methyl esters in a manner analogous to that decribed in Example 18; 1(S),2(R)-diastereoisomer: $[\alpha]_D^{20} = -54.8° \pm 8.7°$ (0.115% in methanol), and 1(R),2(S)-diastereoisomer: IR (CH$_2$Cl$_2$): 3340, 2880, 1615, 1590, 1400, 1340 cm$^{-1}$.

Examples of pharmaceutical compositions and corresponding medicaments in finished form.

There is to be understood hereinafter by the term "active ingredient" a compound of the formula I according to the invention, especially one that is described as a product in Examples 1–41.

EXAMPLE A

An inhalation suspension forming a solid aerosol, containing propellant and 0.1% by weight of active ingredient.

| Composition: | % by weight |
|---|---|
| active ingredient, micronised | 0.1 |
| sorbitan trioleate | 0.5 |
| propellant A (trichlorotrifluoroethane) | 4.4 |
| propellant B | |
| (dichlorodifluoromethane and | 15.0 |
| 1,2-dichlorotetrafluoroethane) | 80.0 |

Manufacture

With the aid of a customary homogeniser, the active ingredient is suspended, with the exclusion of moisture, in trichlorotrifluoroethane with the addition of sorbitan trioleate, and the suspension is introduced into an aerosol container fitted with a dosing valve; the container is sealed and filled up under pressure with propellant B.

EXAMPLE B

An approximately 2% strength aqueous solution of an active ingredient in the form of its sodium or potassium salt, suitable for inhalation.

| Composition | |
|---|---|
| active ingredient (K or Na salt) | 2000 mg |
| disodium salt of ethylenediaminetetraacetic acid | 10 mg |
| benzalkonium chloride | 10 mg |
| water, freshly distilled ad | 100 ml |

Manufacture

The active ingredient is dissolved in approximately 60 ml of freshly distilled water and the stabiliser (disodium salt of ethylenediaminetetraacetic acid) and preservative (benzalkonium chloride) are added. When all the components have completely dissolved, the resulting solution is made up to 100 ml and introduced into small pressurised bottles and these are sealed in gastight manner. The propellant is added as required, in the form of a gas under pressure or in liquid form.

We claim:

1. A compound of the formula

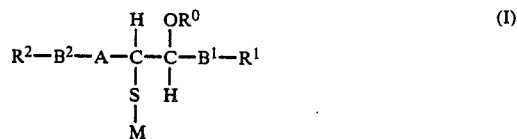

in which the general symbols have the following meanings:

$R^0$ represents hydrogen or $C_{1-7}$-alkanoyl, $R^1$ represents $C_{1-3}$-alkyl which may be substituted by one or more halogen atoms having an atomic number of at most 17, $R^2$ represents an aliphatic radical having from 5 to 15 carbon atoms, A represents a single bond, ethylene or vinylene, $B^1$ represents $C_{1-7}$-alkylene or phenylene, $B^2$ represents a single bond, ethylene or phenylene, M represents an aromatic radical of the partial formula

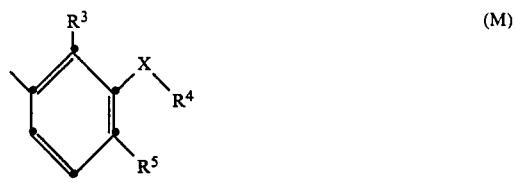

in which the symbols have the following meanings:

$R^3$ represents hydrogen or $C_{1-4}$-alkyl,

X represents NH, O, S or if $R^4$ represents hydrogen, a single bond, one of the symbols $R^4$ and $R^5$ represents hydrogen and the other represents the group —CO—$R^6$, or $R^4$ and $R^5$ together represent the radical —CO—C($R^6$)=C($R^7$)— or —CO—C($R^7$)=C($R^6$)— or $R^4$ and $R^5$, together with X, represent the radical —N=C($R^8$)—C($R^6$)=CH—, in which $R^6$ represents —(CH$_2$)$_b$—COOR$^3$ (in which b=0 to 2)

$R^7$ represents hydrogen or $C_{1-4}$-alkyl and $R^8$ represents hydrogen, methyl, methoxy or halogen, or a physiologically tolerable salt of such a compound having salt-forming properties.

2. A compound according to claim 1, in which, in formula I, the O-atom of the hydroxy group is in the trans-configuration relative to the S-atom.

3. A compound according to claim 1, in which, in formula I, $R^1$ represents trifluoromethyl.

4. A compound according to claim 1, in which, in formula I, $B^1$ represents a linear alkylene group of the partial formula —(CH$_2$)$_a$— in which a represents an integer from 1 to 7.

5. A compound according to claim 1, in which, in formula I, $B^1$ represents unsubstituted phenylene.

6. A compound according to claim 1, in which, in formula I, $R^0$ represents hydrogen.

7. A compound according to claim 1, in which, in formula I, $R^2$-$B^2$-A together represent an o- or p-($C_{5-15}$-alkyl)-phenyl or -styryl group.

8. A compound according to claim 7, in which, in formula I, $R^2$ represents a linear alkyl radical having from 8 to 12 carbon atoms.

9. A compound according to claim 1, in which, in formula I, $R^1$ represents trifluoromethyl, $R^2$-$B^2$-A together represent a linear 1-alkenyl, 1,3-alkadienyl or 1,3,6-alkatrienyl group having from 10 to 16 carbon atoms and $B^1$ represents the radical —$(CH_2)_a$— in which a represents an integer from 3 to 6.

10. A compound according to claim 1, in which, in formula I, M represents a phenyl radical in which $R^3$ represents hydrogen, $R^4$ together with X represents hydrogen and $R^5$ represents the radical —CO—$(CH_2)_b$—COOR$^9$ in which b represents 2 and $R^9$ represents methyl, ethyl or hydrogen.

11. A compound according to claim 1, in which M represents a radical selected from a group consisting of a phenyl radical in which each of $R^3$ and $R^5$ represents hydrogen, X represents the group —NH— and $R^4$ represents the radical —CO—$(CH_2)_b$—COOR$^9$ (in which b represents 1 and $R^9$ represents methyl, ethyl or hydrogen), or a radical of the partial formula

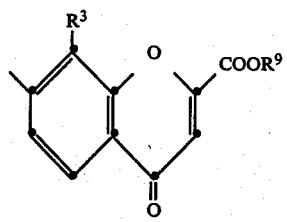

(M$^1$)

in which $R^3$ represents propyl or hydrogen and $R^9$ represents ethyl, methyl or hydrogen, or a radical of the partial formula

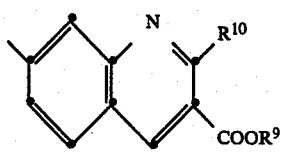

(M$^3$)

in which $R^9$ represents ethyl, methyl or hydrogen and $R^{10}$ represents halogen or methoxy.

12. A compound according to claim 1, in which, in formula I, M represents a radical of the partial formula

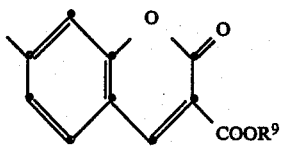

(M$^4$)

in which $R^9$ represents ethyl, methyl or hydrogen.

13. A compound according to claim 11, in which, in formula I, the symbols have the following meanings: $R^0$ represents hydrogen; $R^1$ represents methyl, chloromethyl or trifluoromethyl; $R^2$ represents a linear alkyl radical having from 7 to 15 carbon atoms or a corresponding radical having from 1 to 3 double bonds; A represents cis- or trans-vinylene; $B^1$ represents a linear alkylene group having 2 or 3 carbon atoms; $B^2$ represents a single bond and M has one of the meanings given in claim 11, physiologically tolerable salt thereof.

14. A compound according to claim 11, in which, in formula I, the symbols have the following meanings: $R^0$ represents hydrogen; $R^1$ represents methyl, chloromethyl or trifluoromethyl; $R^2$ represents a linear alkyl radical having from 8 to 12 carbon atoms; A represents a single bond or vinylene in the cis- or trans-configuration; $B^1$ represents a linear alkylene group having 2 or 3 carbon atoms; $B^2$ represents unsubstituted phenylene, and M has one of the meanings given in claim 11, physiologically tolerable salt thereof.

15. A compound according to claim 11, in which, in formula I, the symbols have the following meanings: $R^0$ represents hydrogen; $R^1$ represents methyl, chloromethyl or trifluoromethyl; $R^2$ represents a linear alkyl radical having from 7 to 15 carbon atoms or a corresponding radical having from 1 to 3 double bonds; A represents cis- or trans-vinylene; $B^1$ represents unsubstituted phenylene; $B^2$ represents a single bond and M has one of the meanings given in claim 11, physiologically tolerable salt thereof.

16. A compound according to claim 11, in which, in formula I, the symbols have the following meanings: $R^0$ represents hydrogen; $R^1$ represents methyl, chloromethyl or trifluoromethyl; $R^2$ represents a linear alkyl radical having from 8 to 12 carbon atoms; A represents a single bond or vinylene in the cis- or trans-configuration; $B^1$ represents unsubstituted phenylene; $B^2$ represents unsubstituted phenylene, and M has one of the meanings given in claim 11, physiologically tolerable salt thereof.

17. A compound according to claim 11, in which, in formula I, the symbols have the following meanings: $R^0$ represents hydrogen; $R^1$ represents methyl, chloromethyl or trifluoromethyl; $R^2$ represents a linear $C_{8-12}$-alkyl radical; A represents a transdouble bond; $B^1$ represents unsubstituted m-phenylene; $B^2$ represents unsubstituted phenylene and M has one of the meanings given in claim 11 under partial formula $M^1$, physiologically tolerable salt thereof.

18. A compound according to claim 1 having a free carboxy group, or an alkali metal salt thereof.

19. A pharmaceutical composition comprising as active ingredient at least one of the compounds according to claim 1 together with at least one pharmaceutically acceptable carrier.

20. The pharmaceutical composition according to claim 19 suitable for administration by inhalation.

21. A method of alleviating or eliminating a pathological condition or symptom in a mammal that is attributable to the allergogenic action of a leucotriene or an inflammation comprising administering to said mammal a therapeutically effective amount of a compound of claim 1.

22. The method of claim 21 wherein said pathological condition or symptom is asthma and said mammal is a human being.

* * * * *